United States Patent
Anton et al.

(10) Patent No.: US 11,390,617 B2
(45) Date of Patent: Jul. 19, 2022

(54) METHODS OF TREATING NON-HODGKIN LYMPHOMA USING 2-(2,6-DIOXOPIPERIDIN-3-YL)-4-((2-FLUORO-4-((3-MORPHOLINOAZETIDIN-1-YL)METHYL)BENZYL)AMINO)ISOINDOLINE-1,3-DIONE

(71) Applicant: Celgene Corporation, Summit, NJ (US)

(72) Inventors: Maria Soraya Carrancio Anton, San Diego, CA (US); Tonia J. Buchholz, Moss Beach, CA (US); Antonia Lopez-Girona, San Diego, CA (US); Rama Krishna Narla, San Diego, CA (US); Michael Pourdehnad, San Francisco, CA (US)

(73) Assignee: CELGENE CORPORATION, Summit, NJ (US)

( * ) Notice: Subject to any disclaimer, the term of this patent is extended or adjusted under 35 U.S.C. 154(b) by 128 days.

(21) Appl. No.: 16/844,407

(22) Filed: Apr. 9, 2020

(65) Prior Publication Data

US 2020/0325129 A1 Oct. 15, 2020

Related U.S. Application Data

(60) Provisional application No. 62/833,432, filed on Apr. 12, 2019.

(51) Int. Cl.
*C07D 413/14* (2006.01)
*A61P 35/00* (2006.01)
*C07K 16/28* (2006.01)
*A61K 9/00* (2006.01)

(52) U.S. Cl.
CPC ............ *C07D 413/14* (2013.01); *A61P 35/00* (2018.01); *C07K 16/2887* (2013.01); *A61K 9/0019* (2013.01); *A61K 9/0053* (2013.01)

(58) Field of Classification Search
CPC .................................................... C07D 413/14
USPC ...................................................... 514/210.21
See application file for complete search history.

(56) References Cited

U.S. PATENT DOCUMENTS

2016/0045484 A1    2/2016  Tun et al.

FOREIGN PATENT DOCUMENTS

| WO | WO 2012/177678 A2 | 12/2012 |
| WO | WO 2019/209692 A1 | 10/2019 |

OTHER PUBLICATIONS

ChemicalBook (2017) pp. 1-2.*

* cited by examiner

*Primary Examiner* — Taofiq A Solola
(74) *Attorney, Agent, or Firm* — Jones Day

(57) ABSTRACT

Provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof, alone or in combination with rituximab, for treating, preventing or managing non-Hodgkin lymphoma.

31 Claims, 8 Drawing Sheets

METHODS OF TREATING NON-HODGKIN LYMPHOMA USING 2-(2,6-DIOXOPIPERIDIN-3-YL)-4-((2-FLUORO-4-((3-MORPHOLINOAZETIDIN-1-YL)METHYL)BENZYL)AMINO)ISOINDOLINE-1,3-DIONE

This application claims priority to U.S. Provisional Application No. 62/833,432, filed on Apr. 12, 2019, the entirety of which is incorporated herein by reference.

FIELD

Provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof, alone or in combination with rituximab, for treating, preventing or managing non-Hodgkin lymphoma.

BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and metastasis. Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Current cancer therapy may involve surgery, chemotherapy, hormonal therapy and/or radiation treatment to eradicate neoplastic cells in a patient. Recent advances in cancer therapeutics are discussed by Rajkumar et al. in *Nature Reviews Clinical Oncology* 11, 628-630 (2014).

All of the current cancer therapy approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells.

With respect to chemotherapy, there are a variety of chemotherapeutic agents available for treatment of cancer. A majority of cancer chemotherapeutics act by inhibiting DNA synthesis, either directly or indirectly by inhibiting the biosynthesis of deoxyribonucleotide triphosphate precursors, to prevent DNA replication and concomitant cell division. Gilman et al., Goodman and Gilman's: *The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

Non-Hodgkin lymphoma (NHL), also known as non-Hodgkin's lymphoma, is the fifth most common cancer for both men and women in the United States. An estimated 385,700 patients worldwide were diagnosed with NHL in 2012 and approximately 199,700 patients died as a result of the disease. Torre, L. A. et al. Global cancer statistics, 2012; *CA Cancer J. Clin.* 65, 87-108 (2015). NHL is a heterogeneous disease comprising diverse B-cell and T-cell lymphoma subtypes that collectively make up approximately 4% of all new cancer cases in the United States (U.S.) and account for 3% of cancer-related deaths. Most of NHLs (80% to 90%) are of B-cell origin, and the great majority of the rest are T-cell lymphomas. Common subtypes of NHL include diffuse large B-cell lymphoma (DLBCL), follicular lymphoma (FL), mantle cell lymphoma (MCL), and primary central nervous system lymphoma (PCNSL).

Diffuse large B-cell lymphoma (DLBCL) is the most common subtype of NHL, accounting for up to 30% of newly diagnosed cases, and is clinically classified as an aggressive lymphoma. With the introduction of rituximab plus chemotherapy combination regimens, more than 50% of patients with DLBCL are cured. However, more than 30% of patients in remission will ultimately relapse. For patients who relapse, treatment approaches for second-line DLBCL are less well defined and often are ineffective in achieving long-term disease control. In patients who have received 2 or more lines of therapy and are relapsed and/or refractory and are not candidates for potentially curative therapies due to advanced age or poor performance status, DLBCL remains an incurable disease for which clinical trials are indicated. New therapeutic approaches are still needed.

For follicular lymphoma (FL), the age adjusted incidence rate from 2011-2012 in the U.S. was 3.4 per 100,000. There is no standard treatment for relapsed or refractory (R/R) FL patients. Despite the efforts and advances in front-line treatment, patients with FL continue to experience recurring relapses and require further therapy. The first-line systemic anti-cancer treatments are also considered in second-line therapy; more recently, second-line or later therapy options may include "chemotherapy-free" regimens that are being developed and may become standard of care in the near future. In third-line, patients who fail to respond to a rituximab-containing regimen and have relapsed on or are refractory to additional therapy have limited treatment options and a poor prognosis. There is a high unmet medical need to develop novel treatments for FL patients who fail to respond to standard therapy and whose treatment options for disease remission have been exhausted.

Approximately 6% of all new lymphoma cases each year are mantle cell lymphoma (MCL). The age adjusted incidence rate from 2011-2012 in the U.S. for mantle cell lymphoma (MCL) was 0.8 per 100,000. Despite several available frontline therapies for MCL with prolonged responses, MCL remains an incurable B-cell malignancy. Patients with MCL are often treated with rituximab-chemotherapy combinations, either with or without stem cell transplant consolidation. Relapse is typical, and MCL becomes increasingly resistant to therapy over time.

The age adjusted incidence rate from 2011-2012 in the U.S. for primary central nervous system lymphoma (PCNSL) was 0.3 per 100,000. Despite high response rates with initial high-dose methotrexate (HD-MTX)-based regimens, more than half of the responders relapse. Once PCNSL has relapsed, prognosis remains poor. Novel therapeutic agents with CNS penetration, better efficacy, and tolerable toxicity profile are urgently needed.

There remains a significant need for safe and effective methods of treating, preventing and managing NHL, particularly for NHL that is refractory to standard treatments, such as surgery, radiation therapy, chemotherapy and hormonal therapy, while reducing or avoiding the toxicities and/or side effects associated with conventional therapies.

Citation or identification of any reference in this section of this application is not to be construed as an admission that the reference is prior art to the present application.

SUMMARY

Provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof, alone or in combination with rituximab, for treating, preventing or managing NHL.

In certain embodiments, provided herein is a method of treating NHL, comprising administering to a subject in need thereof a therapeutically effective amount of Compound 1 of the formula:

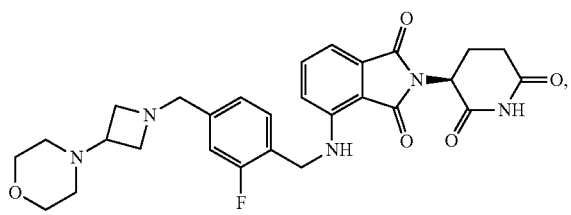

1 or a tautomer, isotopolog, or pharmaceutically acceptable salt thereof.

In certain embodiments, provided herein is a method of treating NHL, comprising administering to a subject in need thereof a therapeutically effective amount of Compound 2 of the formula:

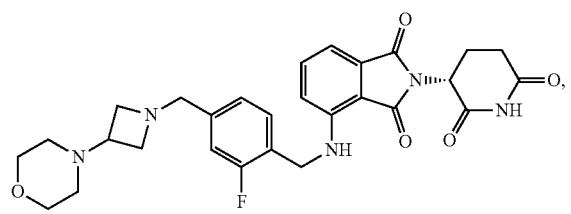

2 or a tautomer, isotopolog, or pharmaceutically acceptable salt thereof.

In certain embodiments, provided herein is a method of treating NHL, comprising administering to a subject in need thereof a therapeutically effective amount of Compound 3 of the formula:

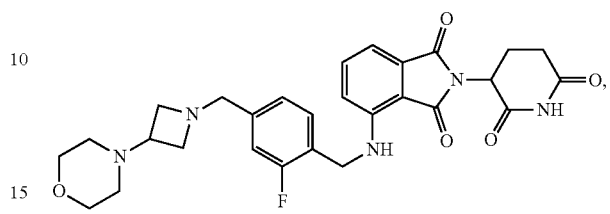

3 or an enantiomer, mixture of enantiomers, tautomer, isotopolog, or pharmaceutically acceptable salt thereof.

In certain embodiments, the NHL is not diffuse large B-cell lymphoma (DLBCL).

In certain embodiments, the NHL is diffuse large B-cell lymphoma (DLBCL), follicular lymphoma (FL), mantle cell lymphoma (MCL), or primary central nervous system lymphoma (PCNSL).

In certain embodiments, the methods provided herein further comprising administering to the subject a therapeutically effective amount of rituximab.

The present embodiments can be understood more fully by reference to the detailed description and examples, which are intended to exemplify non-limiting embodiments.

DETAILED DESCRIPTION

Definitions

Figure 1:
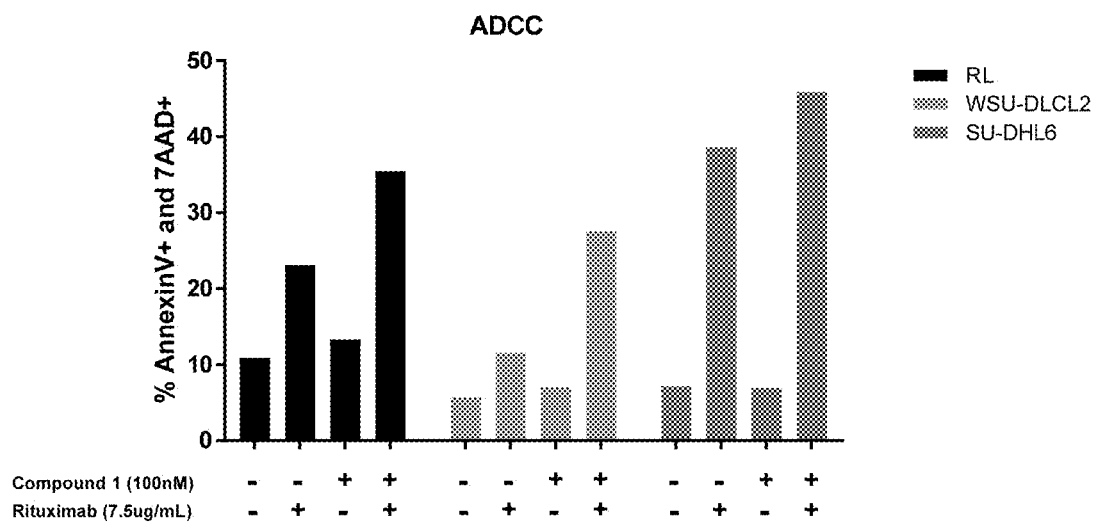
FIG. 1 illustrates NK-mediated cell killing of the combination of Compound 1 and rituximab in lymphoma cell lines WSU-DLCL2, SU-DHL6, and RL.

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein, and in the specification and the accompanying claims, the indefinite articles "a" and "an" and the definite article "the" include plural as well as single referents, unless the context clearly indicates otherwise.

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of a compound provided herein include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Others are well-known in the art, see for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995).

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds can have chiral centers and can occur as racemates, individual enantiomers or diastereomers, and mixtures thereof. All such isomeric forms are included within the embodiments provided herein, including mixtures thereof.

The use of stereomerically pure forms of such compounds, as well as the use of mixtures of those forms, are encompassed by the embodiments provided herein. For example, mixtures comprising equal or unequal amounts of the enantiomers of a particular compound may be used in methods and compositions provided herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. *L., Stereochemistry of Carbon Compounds* (McGraw-Hill, N Y, 1962); Wilen, S. H., *Tables of Resolving Agents and Optical Resolutions* p. 268 (E. L. Eliel, Ed., Univ. of Notre Dame Press, Notre Dame, Ind., 1972); Todd, M., *Separation Of Enantiomers: Synthetic Methods* (Wiley-VCH Verlag GmbH & Co. KGaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuj a, S., *Chiral Separation Methods for Pharmaceutical and Biotechnological Products* (John Wiley & Sons, 2011).

It is to be understood that the compounds provided herein may contain chiral centers. Such chiral centers may be of either the (R) or (S) configuration, or may be a mixture thereof. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as chromatography on a chiral stationary phase.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

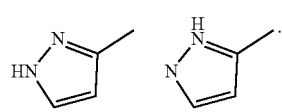

As readily understood by one skilled in the art, a wide variety of functional groups and other structures may exhibit tautomerism and all tautomers of a compound are within the scope of the compound as provided herein.

It should also be noted that a compound provided herein can contain unnatural proportions of atomic isotopes at one or more of the atoms. For example, the compounds may be radiolabeled with radioactive isotopes, such as for example tritium (H), iodine-125 ($^{125}$I) sulfur-35 ($^{35}$S), or carbon-14 ($^{14}$C), or may be isotopically enriched, such as with deuterium (2H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of a compound, whether radioactive or not, are intended to be encompassed within the scope of the compound as provided herein. In some embodiments, provided herein are isotopologues of the compounds, for example, the isotopologues are deuterium, carbon-13 ($^{13}$C), and/or nitrogen-15 ($^{15}$N) enriched compounds. As used herein, "deuterated", means a compound wherein at least one hydrogen (H) has been replaced by deuterium (indicated by D or $^2$H), that is, the compound is enriched in deuterium in at least one position.

It is understood that, independently of stereomerical or isotopic composition, each compound provided herein can be provided in the form of any of the pharmaceutically acceptable salts provided herein. Equally, it is understood that the isotopic composition may vary independently from the stereomerical composition of each compound provided herein. Further, the isotopic composition, while being restricted to those elements present in the respective compound or salt thereof, may otherwise vary independently from the selection of the pharmaceutically acceptable salt of the respective compound.

It should be noted that if there is a discrepancy between a depicted structure and a name for that structure, the depicted structure is to be accorded more weight.

As used herein and unless otherwise indicated, the term "treating" means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself.

As used herein and unless otherwise indicated, the term "preventing" means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition.

As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein and unless otherwise indicated, the term "effective amount" in connection with a compound means an amount capable of treating, preventing, or managing a disorder, disease or condition, or symptoms thereof.

As used herein and unless otherwise indicated, the term "subject" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human.

As used herein and unless otherwise indicated, the term "relapsed" refers to a disorder, disease, or condition that responded to treatment (e.g., achieved a complete response) then had progression. The treatment can include one or more lines of therapy.

In one embodiment, "relapsed" DLBCL may refer to DLBCL that has been previously treated with one or more lines of therapy. In one embodiment, the relapsed DLBCL is DLBCL that has been previously treated with one, two, three or four lines of therapy. In one embodiment, the relapsed DLBCL is DLBCL that has been previously treated with two or more lines of treatment.

In one embodiment, "relapsed" FL may refer to FL that has been previously treated with one or more lines of therapy. In one embodiment, the relapsed FL is FL that has been previously treated with one, two, three or four lines of therapy. In one embodiment, the relapsed FL is FL that has been previously treated with two or more lines of treatment.

As used herein and unless otherwise indicated, the term "refractory" refers to a disorder, disease, or condition that has not responded to prior treatment that can include one or more lines of therapy. In one embodiment, the disorder, disease, or condition has been previously treated one, two, three or four lines of therapy. In one embodiment, the disorder, disease, or condition has been previously treated with two or more lines of treatment, and has less than a complete response (CR) to most recent systemic therapy containing regimen.

In the context of a cancer, inhibition may be assessed by inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP as used herein means the time from treatment onset until tumor progression; TTP does not include deaths. In one embodiment, PFS means the time from treatment onset until tumor progression or death. In one embodiment, PFS means the time from the first dose of compound to the first occurrence of disease progression or death from any cause. In one embodiment, PFS rates is computed using the Kaplan-Meier estimates. Event-free survival (EFS) means the time from treatment onset until any treatment failure, including disease progression, treatment discontinuation for any reason, or death. In one embodiment, overall response rate (ORR) means the percentage of patients who achieve a response. In one embodiment, ORR means the sum of the percentage of patients who achieve complete and partial responses. In one embodiment, ORR means the percentage of patients whose best response ≥partial response (PR). In one embodiment, duration of response (DoR) is the time from achieving a response until relapse or disease progression. In one embodiment, DoR is the time from achieving a response ≥partial response (PR) until relapse or disease progression. In one embodiment, DoR is the time from the first documentation of a response until to the first documentation of progressive disease or death. In one embodiment, DoR is the time from the first documentation of a response ≥partial response (PR) until to the first documentation of progressive disease or death. In one embodiment, time to response (TTR) means the time from the first dose of compound to the first documentation of a response. In one embodiment, TTR means the time from the first dose of compound to the first documentation of a response ≥partial response (PR). In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of NHL may be assessed by the International Workshop Criteria for Malignant Lymphoma (see Cheson et al., *J. Clin. Oncol.* 2014, 32(27):3059-3068) and the Deauville Criteria for fluorodeoxyglucose-positron emission tomography (FDG-PET) scan interpretation (Itti et al., *Eur. J. Nucl. Med. Mol. Imaging,* 2013, 40(9):1312-20; Meignan et al., *Leuk Lymphoma,* 2014, 55(1):31-37) ("Lugano criteria"), using the response and end point definition shown in Tables 1-3.

TABLE 1

Criteria for Involvement of Site.

| Tissue Site | Clinical | FDG Avidity | Test | Positive Finding |
|---|---|---|---|---|
| Lymph nodes | Palpable | FDG-avid histologies | PET/CT | Increase FDG uptake |
| | | Nonavid disease | CT | Unexplained node enlargement |
| Spleen | Palpable | FDG-avid histologies | PET/CT | Diffuse uptake, solitary mass, miliary lesions, nodules |
| | | Nonavid disease | CT | >13 cm in vertical length, mass, nodules |
| Liver | Palpable | FDG-avid histologies | PET/CT | Diffuse uptake, mass |
| | | Nonavid disease | CT | Nodules |
| CNS | Signs, symptoms | N/A | CT | Mass lesion(s) |
| | | | MRI | Leptomeningeal infiltration, mass lesions |
| | | | CSF assessment | Cytology, flow cytometry |
| Other (eg, skin, lung, GI tract, bone, bone marrow) | Site dependent | N/A | PET/CT[a], biopsy | Lymphoma involvement |

CNS = central nervous system;
CSF = cerebrospinal fluid;
CT = computed tomography;
FDG = fluorodeoxyglucose;
GI = gastrointestinal;
MRI = magnetic resonance imaging;
PET = positron emission tomography;
N/A = not applicable.
[a]PET/CT is adequate for determination of bone marrow involvement and can considered highly suggestive for involvement of other extralymphatic sites. Biopsy confirmation of those sites can be considered if necessary.

TABLE 2

Lugano Response Criteria for Non-Hodgkin Lymphoma.

| Response | Site | PET/CT (metabolic response) | CT (Radiologic response) |
|---|---|---|---|
| Complete response | Lymph nodes and extralymphatic sites | Score 1, 2, 3 with or without residual mass on 5-PS (Table 3) | All of the following:<br>Target nodes/nodal masses must regress to ≤1.5 cm in LDi<br>No extralymphatic sites of disease |
| | Non-measured lesion | N/A | Absent |
| | Organ enlargement | N/A | Regress to normal |
| | New Lesions | None | None |
| | Bone Marrow | No evidence of FDG-avid disease in marrow | Normal by morphology; if indeterminate, IHC negative[a] |

TABLE 2-continued

Lugano Response Criteria for Non-Hodgkin Lymphoma.

| Response | Site | PET/CT (metabolic response) | CT (Radiologic response) |
|---|---|---|---|
| Partial Response | Lymph nodes and extralymphatic sites | Score 4 or 5 on 5-PS with reduced uptake compared with baseline and residual mass(es) of any size At interim these findings suggest responding disease At end of treatment these findings may indicate residual disease | All of the following: ≥50% decrease in SPD of up to 6 target measureable nodes and extranodal sites When a lesion is too small to measure on CT, assign 5 mm × 5 mm as the default value When no longer visible, 0 mm × 0 mm For a node >5 mm × 5 mm, but smaller than normal, use actual measurement for calculation |
| | Non-measured lesion | N/A | Absent/normal, regressed, but no increase |
| | Organ enlargement | N/A | Spleen must have regressed by >50% in length beyond normal |
| | New Lesions | None | None |
| | Bone Marrow | Residual uptake higher than uptake in normal marrow but reduced compared with baseline. If persistent focal changes in the marrow in the context of nodal response, consider MRI or biopsy or interval scan | N/A |
| Stable Disease | Target nodes/nodal masses, extranodal lesions | Score 4 or 5 on 5-PS with no significant change in FDG uptake from baseline | <50% decrease from baseline of up to 6 dominant, measureable nodes and extranodal sites No criteria for progressive disease are met |
| | Non-measured lesion | N/A | No increase consistent with progression |
| | Organ enlargement | N/A | No increase consistent with progression |
| | New Lesions | None | None |
| | Bone Marrow | No change from baseline | N/A |
| Progressive Disease | Lymph nodes and extralymphatic sites | Score 4 or 5 on 5-PS with an increase in intensity of uptake compared with baseline and/or New FDG-avid foci consistent with lymphoma | At least one of the following: PPD progression: An individual node/lesion must be abnormal with: LDi >1.5 cm and Increase by ≥50% from PPD nadir and An increase in LDi or SDi from nadir 0.5 cm for lesions ≤2 cm 1.0 cm for lesions >2 cm In the setting of splenomegaly, splenic length must increase by >50% of the extent of its prior increase above baseline (eg, a 15 cm spleen must increase to >16 cm). If no splenomegaly, must increase by at least 2 cm from baseline must increase by at least 2 cm from baseline New or recurrent splenomegaly |
| | Non-measured lesion | None | New or clear progression of preexisting nonmeasured lesions |
| | New Lesions | New FDG-avid foci consistent with lymphoma rather than another etiology (eg, infection, inflammation). If uncertain etiology, consider biopsy or interval scan | Regrowth of previously resolved lesions A new node >1.5 cm in any axis A new extranodal site >1.0 cm in any axis; if <1.0 cm in any axis, its presence must be unequivocal and must be attributable to lymphoma Assessable disease of any size unequivocally attributable to lymphoma |
| | Bone Marrow | New of recurrent FDG-avid foci | New or recurrent involvement |

CMR = complete metabolic response;
LDi = longest transverse diameter of a lesion;
PPD = cross product of the LDi and perpendicular diameter;
SDi = shortest axis perpendicular to the LDi;
SPD = sum of the product of the perpendicular diameters for multiple lesions;
N/A = not applicable.
[a]Required for CR if bone marrow involvement at baseline
[b]In Waldeyer's ring or extranodal sites with high physiologic uptake or with activation within spleen or marrow; (eg with chemotherapy or myeloid colony stimulating factors), uptake may be greater than normal mediastinum and/or liver. In this circumstance, CMR may be inferred if uptake at sites of initial involvement is no greater than surrounding normal tissue.
[c]FDG-avid lymphomas should have response assessed by PET-CT. Some diseases can typically be followed with CT alone (ie, marginal zone lymphoma).
[d]PET should be done with contrast-enhanced diagnostic CT and can be done simultaneously or at separate procedures.

TABLE 3

PET Five Point Scale (5-PS).

| | |
|---|---|
| 1 | No uptake above background |
| 2 | Uptake ≤ mediastinum |
| 3 | Uptake > mediastinum but ≤ liver |
| 4 | Uptake moderately > liver |
| 5 | Uptake markedly higher than liver and/or new lesions |
| X | New areas of uptake unlikely to be related to lymphoma |

<sup>a</sup>The Deauville five-point scale (5PS) is an internationally recommended scale for clinical routine and clinical trials using FDG-PET/CT in the initial staging and assessment of treatment response in Hodgkin lymphoma (HL) and certain types of non-Hodgkin lymphomas (NHL).

In certain embodiments, stable disease or lack thereof can be determined by methods known in the art such as evaluation of patient symptoms, physical examination, visualization of the tumor that has been imaged, for example using FDG-PET (fluorodeoxyglucose positron emission tomography), PET/CT (positron emission tomography/computed tomography) scan, MRI (magnetic resonance imaging) Brain/Spine, CSF (cerebrospinal fluid), ophthalmologic exams, vitreal fluid sampling, retinal photograph, bone marrow evaluation and other commonly accepted evaluation modalities.

As used herein and unless otherwise indicated, the terms "co-administration" and "in combination with" include the administration of one or more therapeutic agents (for example, a compound provided herein and another anti-NIL agent, cancer agent or supportive care agent) either simultaneously, concurrently or sequentially with no specific time limits. In one embodiment, the agents are present in the cell or in the patient's body at the same time or exert their biological or therapeutic effect at the same time. In one embodiment, the therapeutic agents are in the same composition or unit dosage form. In another embodiment, the therapeutic agents are in separate compositions or unit dosage forms.

The term "supportive care agent" refers to any substance that treats, prevents or manages an adverse effect from treatment with another therapeutic agent.

The term "about," as used herein, unless otherwise indicated, refers to a value that is no more than 10% above or below the value being modified by the term. For example, the term "about 10 mg/m²" means a range of from 9 mg/m² to 11 mg/m².

Compounds

Also provided for use in the methods provided herein is the compound (S)-2-(2,6-dioxopiperidin-3-yl)-4-((2-fluoro-4-((3-morpholinoazetidin-1-yl)methyl)benzyl)amino)isoindoline-1,3-dione, referred to as "Compound 1":

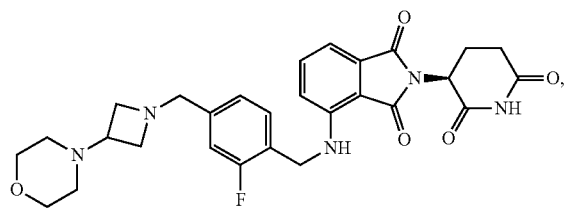

or a tautomer, isotopolog, or pharmaceutically acceptable salt thereof.

Also provided for use in the methods provided herein is the compound (R)-2-(2,6-dioxopiperidin-3-yl)-4-((2-fluoro-4-((3-morpholinoazetidin-1-yl)methyl)benzyl)amino)isoindoline-1,3-dione, referred to as "Compound 2":

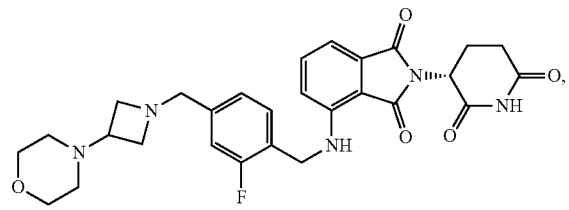

or a tautomer, isotopolog, or pharmaceutically acceptable salt thereof.

Provided for use in the methods provided herein is the compound 2-(2,6-dioxopiperidin-3-yl)-4-((2-fluoro-4-((3-morpholinoazetidin-1-yl)methyl)benzyl)amino)isoindoline-1,3-dione, referred to as "Compound 3":

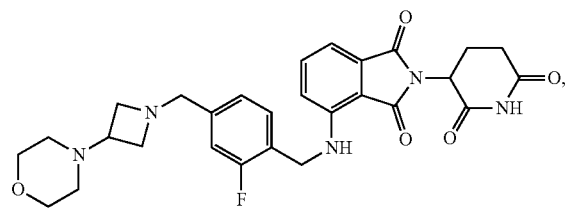

or an enantiomer, mixture of enantiomers, tautomer, isotopolog, or pharmaceutically acceptable salt thereof.

In one embodiment, Compound 1 is used in the methods provided herein. In one embodiment, a tautomer of Compound 1 is used in the methods provided herein. In one embodiment, an isotopolog of Compound 1 is used in the methods provided herein. In one embodiment, a pharmaceutically acceptable salt of Compound 1 is used in the methods provided herein.

In one embodiment, Compound 2 is used in the methods provided herein. In one embodiment, a tautomer of Compound 2 is used in the methods provided herein. In one embodiment, an isotopolog of Compound 2 is used in the methods provided herein. In one embodiment, a pharmaceutically acceptable salt of Compound 2 is used in the methods provided herein.

In one embodiment, Compound 3 is used in the methods provided herein. In one embodiment, an enantiomer of Compound 3 is used in the methods provided herein. In one embodiment, a mixture of enantiomers of Compound 3 is used in the methods provided herein. In one embodiment, a tautomer of Compound 3 is used in the methods provided herein. In one embodiment, an isotopolog of Compound 3 is used in the methods provided herein. In one embodiment, a pharmaceutically acceptable salt of Compound 3 is used in the methods provided herein.

Methods of Treatment and Prevention

In one embodiment, provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof, alone or in combination with rituximab, for treating, preventing or managing non-Hodgkin lymphoma (NHL).

In one embodiment, provided herein is a method of treating NHL, comprising administering to a subject in need thereof a therapeutically effective amount of Compound 1 of the formula:

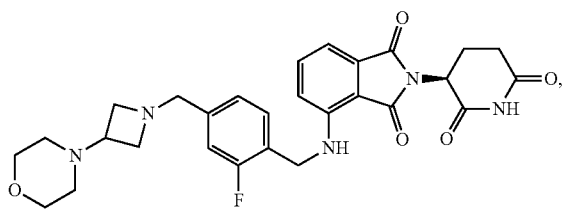

1 or a tautomer, isotopolog, or pharmaceutically acceptable salt thereof. In one embodiment, provided herein is a method of treating NHL that is not diffuse large B-cell lymphoma (DLBCL), comprising administering to a subject in need thereof a therapeutically effective amount of Compound 1 or a tautomer, isotopolog, or pharmaceutically acceptable salt thereof.

In one embodiment, provided herein is a method of treating NHL, comprising administering to a subject in need thereof a therapeutically effective amount of Compound 2 of the formula:

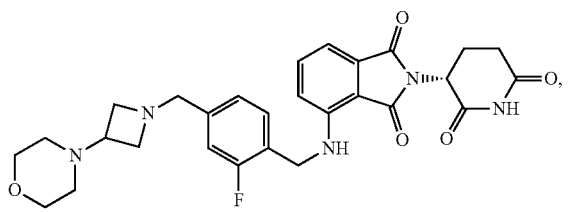

2 or a tautomer, isotopolog, or pharmaceutically acceptable salt thereof. In one embodiment, provided herein is a method of treating NHL that is not DLBCL, comprising administering to a subject in need thereof a therapeutically effective amount of Compound 2 or a tautomer, isotopolog, or pharmaceutically acceptable salt thereof.

In one embodiment, provided herein is a method of treating NHL, comprising administering to a subject in need thereof a therapeutically effective amount of Compound 3 of the formula:

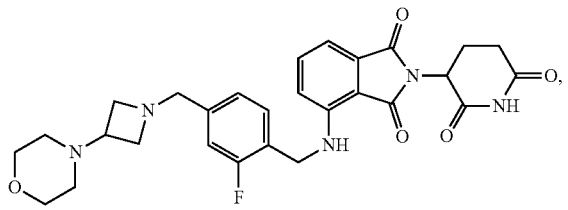

3 or an enantiomer, mixture of enantiomers, tautomer, isotopolog, or pharmaceutically acceptable salt thereof. In one embodiment, provided herein is a method of treating NHL that is not DLBCL, comprising administering to a subject in need thereof a therapeutically effective amount of Compound 3 or an enantiomer, mixture of enantiomers, tautomer, isotopolog, or pharmaceutically acceptable salt thereof.

In one embodiment, provided herein is a method of preventing NHL, which comprises administering to a subject in need thereof a therapeutically effective amount of Compound 1, or a tautomer, isotopolog, or pharmaceutically acceptable salt thereof. In one embodiment, provided herein is a method of preventing NHL, which comprises administering to a subject in need thereof a therapeutically effective amount of Compound 2, or a tautomer, isotopolog, or pharmaceutically acceptable salt thereof. In one embodiment, provided herein is a method of preventing NHL, which comprises administering to a subject in need thereof a therapeutically effective amount of Compound 3, or an enantiomer, mixture of enantiomers, tautomer, isotopolog, or pharmaceutically acceptable salt thereof. In one embodiment, provided herein is a method of preventing NHL that is not DLBCL, which comprises administering to a subject in need thereof a therapeutically effective amount of Compound 1, or a tautomer, isotopolog, or pharmaceutically acceptable salt thereof. In one embodiment, provided herein is a method of preventing NHL that is not DLBCL, which comprises administering to a subject in need thereof a therapeutically effective amount of Compound 2, or a tautomer, isotopolog, or pharmaceutically acceptable salt thereof. In one embodiment, provided herein is a method of preventing NHL that is not DLBCL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of managing NHL, which comprises administering to a subject in need thereof a therapeutically effective amount of Compound 1, or a tautomer, isotopolog, or pharmaceutically acceptable salt thereof. In one embodiment, provided herein is a method of managing NHL, which comprises administering to a subject in need thereof a therapeutically effective amount of Compound 2, or a tautomer, isotopolog, or pharmaceutically acceptable salt thereof. In one embodiment, provided herein is a method of managing NHL, which comprises administering to a subject in need thereof a therapeutically effective amount of Compound 3, or an enantiomer, mixture of enantiomers, tautomer, isotopolog, or pharmaceutically acceptable salt thereof. In one embodiment, provided herein is a method of managing NHL that is not DLBCL, which comprises administering to a subject in need thereof a therapeutically effective amount of Compound 1, or a tautomer, isotopolog, or pharmaceutically acceptable salt thereof. In one embodiment, provided herein is a method of managing NHL that is not DLBCL, which comprises administering to a subject in need thereof a therapeutically effective amount of Compound 2, or a tautomer, isotopolog, or pharmaceutically acceptable salt thereof. In one embodiment, provided herein is a method of managing NHL that is not DLBCL, which comprises administering to a subject in need thereof a therapeutically effective amount of Compound 3, or an enantiomer, mixture of enantiomers, tautomer, isotopolog, or pharmaceutically acceptable salt thereof.

In certain embodiments, the NHL is not a diffuse large B-cell lymphoma (DLBCL).

In certain embodiments, the NHL is DLBCL. In one embodiment, the DLBCL is primary DLBCL. In one embodiment, the DLBCL is activated B-cell-like DLBCL (ABC-DLBCL). In one embodiment, the DLBCL is germinal center B-cell-like DLBCL (GCB-DLBCL). In one embodiment, the DLBCL is unclassified DLBCL. In one embodiment, the DLBCL is primary mediastinal B-cell type DLBCL (PMBL DLBCL). In one embodiment, the DLBCL is double-hit DLBCL (DHIT DLBCL), also referred to as cMyc/Bcl-2 mutant DLBCL. In one embodiment, the DLBCL is triple-hit DLBCL (THIT DLBCL) also referred to as cMyc/Bcl2/Bcl6 rearrangement DLBCL.

In certain embodiments, the NHL is follicular lymphoma (FL).

In other embodiments, the NHL is mantle cell lymphoma (MCL).

In yet other embodiments, the NHL is primary central nervous system lymphoma (PCNSL).

In certain embodiments, the NHL is relapsed or refractory NHL. In one embodiment, the NHL is relapsed NHL. In one embodiment, the NHL is refractory NHL. In one embodiment, the relapsed or refractory NHL is not relapsed or refractory DLBCL.

In certain embodiments, the NHL subject has radiological evidence of progression after achieving a complete response (CR). In certain embodiments, the NHL subject has achieved less than a CR to most recent systemic therapy containing regimen, and has radiological evidence of active disease or disease progression or recurrence in less than or equal to 12 months of prior stem cell transplantation (SCT).

In certain embodiments, the NHL subject has failed one or more lines of therapy and is not a candidate for other therapy. In certain embodiments, the subject has received at least one prior therapy and is not eligible for any therapy other than the methods of treatment described herein. In certain embodiments, the subject has relapsed after or progressed on standard anticancer therapy.

In certain embodiments, the subject has failed at least one prior therapy. In certain embodiments, the subject has failed at least two prior therapies.

In one embodiment, the NHL is relapsed or refractory DLBCL. In one embodiment, the DLBCL is relapsed DLBCL. In one embodiment, the DLBCL is refractory DLBCL. In one embodiment, the DLBCL is refractory to doxorubicin. In one embodiment, the DLBCL is resistant to doxorubicin.

In one embodiment, the DLBCL is treated with two or more prior lines of treatment.

In one embodiment, the DLBCL is transformed lymphoma. In another embodiment, the DLBCL is not otherwise specified (NOS) DLBCL.

In one embodiment, the NHL is relapsed or refractory FL. In one embodiment, the FL is relapsed FL. In one embodiment, the FL is refractory FL.

In one embodiment, the FL is treated with one or more prior lines of treatment. In one embodiment, the FL is treated with two or more prior lines of treatment.

In one embodiment, the NHL is relapsed or refractory MCL. In one embodiment, the MCL is relapsed MCL. In one embodiment, the MCL is refractory MCL.

In one embodiment, the MCL is treated with one or more prior lines of treatment. In one embodiment, the MCL is treated with two or more prior lines of treatment.

In one embodiment, the NHL is relapsed or refractory PCNSL. In one embodiment, the PCNSL is relapsed PCNSL. In one embodiment, the PCNSL is refractory PCNSL.

In certain embodiments, the NHL is newly diagnosed NHL. In certain embodiments, the NHL is newly diagnosed NHL that is not diffuse large B-cell lymphoma. In certain embodiments, the NHL is newly diagnosed diffuse large B-cell lymphoma. In certain embodiments, the NHL is newly diagnosed follicular lymphoma. In certain embodiments, the NHL is newly diagnosed mantle cell lymphoma. In certain embodiments, the NHL is newly diagnosed primary central nervous system lymphoma.

In certain embodiments, the methods provided herein further comprise administering to the subject a therapeutically effective amount of rituximab.

In one embodiment, a first therapy (e.g., a prophylactic or therapeutic agent such as Compound 1, Compound 2 or Compound 3, or an enantiomer, mixture of enantiomers, tautomer, isotopolog, or pharmaceutically acceptable salt thereof) provided herein is administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before) to the administration of a second therapy (e.g., rituximab) to the subject.

In one embodiment, a first therapy (e.g., a prophylactic or therapeutic agent such as Compound 1, Compound 2 or Compound 3, or an enantiomer, mixture of enantiomers, tautomer, isotopolog, or pharmaceutically acceptable salt thereof) provided herein is administered concomitantly with the administration of a second therapy (e.g., rituximab) to the subject.

In one embodiment, a first therapy (e.g., a prophylactic or therapeutic agent such as Compound 1, Compound 2 or Compound 3, or an enantiomer, mixture of enantiomers, tautomer, isotopolog, or pharmaceutically acceptable salt thereof) provided herein is administered subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., rituximab) to the subject.

In certain embodiments, rituximab is administered according to the locally approved label or Pharmacy manual for preparation, administration, and storage information. In certain embodiments, rituximab is administered intravenously. In certain embodiments, rituximab is administered subcutaneously. In certain embodiments, rituximab is administered via IV injection or IV infusion. In certain embodiments, rituximab is administered via IV infusion.

In one embodiment, a compound described herein, e.g., Compound 1, Compound 2 or Compound 3, or an enantiomer, mixture of enantiomers, tautomer, isotopolog, or pharmaceutically acceptable salt thereof, is administered at a dose of from about 0.1 mg to about 1.6 mg per day. In one embodiment, the compound is administered at a dose of from about 0.1 mg to about 1.2 mg per day. In one embodiment, the compound is administered at a dose of from about 0.1 mg to about 0.8 mg per day. In one embodiment, the compound is administered at a dose of from about 0.1 mg to about 0.6 mg per day. In one embodiment, the compound is administered at a dose of from about 0.1 mg to about 0.4 mg per day. In one embodiment, the compound is administered at a dose of from about 0.1 mg to about 0.2 mg per day. In one embodiment, the compound is administered at a dose of from about 0.2 mg to about 1.6 mg per day. In one embodiment, the compound is administered at a dose of from about 0.2 mg to about 1.2 mg per day. In one embodiment, the compound is administered at a dose of from about 0.2 mg to about 0.8 mg per day. In one embodiment, the compound is administered at a dose of from about 0.2 mg to about 0.6 mg per day. In one embodiment, the compound is administered at a dose of from about 0.2 mg to about 0.4 mg per day. In one embodiment, the compound is administered at a dose of from about 0.4 mg to about 1.6 mg per day. In one embodiment, the compound is administered at a dose of from about 0.4 mg to about 1.2 mg per day. In one embodiment, the compound is administered at a dose of from about 0.4 mg to about 0.8 mg per day. In one embodiment, the compound is administered at a dose of from about 0.4 mg to about 0.6 mg per day. In one embodiment, the compound is administered at a dose of from about 0.6 mg to about 1.6 mg per day. In one embodiment, the compound is administered at a dose of from about 0.6 mg to about 1.2 mg per day. In one embodiment, the compound is administered at a dose of from about 0.6 mg to about 0.8 mg per day. In one embodiment, the compound is administered at a dose of from about 0.8 mg to about 1.6 mg per day. In one embodiment, the compound is administered at a dose of from about 0.8 mg to about 1.2 mg per day. In one embodiment, the compound is administered at a dose of from about 1.2 mg to about 1.6 mg per day.

In certain embodiments, a compound described herein, e.g., Compound 1, Compound 2 or Compound 3, or an enantiomer, mixture of enantiomers, tautomer, isotopolog, or pharmaceutically acceptable salt thereof, is administered at a dose of about 0.1 mg, about 0.2 mg, about 0.4 mg, about 0.6 mg, about 0.8 mg, about 1.2 mg, or about 1.6 mg per day. In certain embodiments, the compound is administered at a dose of about 0.1 mg per day. In certain embodiments, the compound is administered at a dose of about 0.2 mg per day. In certain embodiments, the compound is administered at a dose of about 0.4 mg per day. In certain embodiments, the compound is administered at a dose of about 0.6 mg per day. In certain embodiments, the compound is administered at a dose of about 0.8 mg per day. In certain embodiments, the compound is administered at a dose of about 1.2 mg per day. In certain embodiments, the compound is administered at a dose of about 1.6 mg per day.

In certain embodiments, rituximab is administered at an amount according to the physician's decision. In certain embodiments, rituximab is administered once or twice daily. In certain embodiments, rituximab is administered in an amount of from about 50 to about 1000 mg/m$^2$, from about 100 to about 750 mg/m$^2$, from about 250 to about 500 mg/m$^2$, or from about 300 to about 400 mg/m$^2$. In certain embodiments, rituximab is administered in an amount of 375 mg/m$^2$ per day.

In one embodiment, provided herein is a method of treating DLBCL, which comprises administering to a subject in need thereof a therapeutically effective amount of Compound 1, or a tautomer, isotopolog, or pharmaceutically acceptable salt thereof. In one embodiment, the method further comprises administering to the subject a therapeutically effective amount of rituximab.

In one embodiment, provided herein is a method of treating DLBCL, which comprises administering to a subject in need thereof a therapeutically effective amount of Compound 2, or a tautomer, isotopolog, or pharmaceutically acceptable salt thereof. In one embodiment, the method further comprises administering to the subject a therapeutically effective amount of rituximab.

In one embodiment, provided herein is a method of treating DLBCL, which comprises administering to a subject in need thereof a therapeutically effective amount of Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of preventing DLBCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In another embodiment, provided herein is a method of managing DLBCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of treating FL, which comprises administering to a subject in need thereof a therapeutically effective amount of Compound 1, or a tautomer, isotopolog, or pharmaceutically acceptable salt thereof. In one embodiment, the method further comprises administering to the subject a therapeutically effective amount of rituximab.

In one embodiment, provided herein is a method of treating FL, which comprises administering to a subject in need thereof a therapeutically effective amount of Compound 2, or a tautomer, isotopolog, or pharmaceutically acceptable salt thereof. In one embodiment, the method further comprises administering to the subject a therapeutically effective amount of rituximab.

In one embodiment, provided herein is a method of treating FL, which comprises administering to a subject in need thereof a therapeutically effective amount of Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of preventing FL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In another embodiment, provided herein is a method of managing FL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of treating MCL, which comprises administering to a subject in need thereof a therapeutically effective amount of Compound 1, or a tautomer, isotopolog, or pharmaceutically acceptable salt thereof. In one embodiment, the method further comprises administering to the subject a therapeutically effective amount of rituximab.

In one embodiment, provided herein is a method of treating MCL, which comprises administering to a subject in need thereof a therapeutically effective amount of Compound 2, or a tautomer, isotopolog, or pharmaceutically acceptable salt thereof. In one embodiment, the method further comprises administering to the subject a therapeutically effective amount of rituximab.

In one embodiment, provided herein is a method of treating MCL, which comprises administering to a subject in need thereof a therapeutically effective amount of Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of preventing MCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In another embodiment, provided herein is a method of managing MCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of treating PCNSL, which comprises administering to a subject in need thereof a therapeutically effective amount of Compound 1, or a tautomer, isotopolog, or pharmaceutically acceptable salt thereof. In one embodiment, the method further comprises administering to the subject a therapeutically effective amount of rituximab.

In one embodiment, provided herein is a method of treating PCNSL, which comprises administering to a subject in need thereof a therapeutically effective amount of Compound 2, or a tautomer, isotopolog, or pharmaceutically acceptable salt thereof. In one embodiment, the method further comprises administering to the subject a therapeutically effective amount of rituximab.

In one embodiment, provided herein is a method of treating PCNSL, which comprises administering to a subject in need thereof a therapeutically effective amount of Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of preventing PCNSL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In another embodiment, provided herein is a method of managing PCNSL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of treating relapsed or refractory DLBCL, which comprises administering to a subject in need thereof a therapeutically effective amount of Compound 1, or a tautomer, isotopolog, or pharmaceutically acceptable salt thereof. In one embodiment, the method further comprises administering to the subject a therapeutically effective amount of rituximab.

In one embodiment, provided herein is a method of treating relapsed or refractory DLBCL, which comprises administering to a subject in need thereof a therapeutically effective amount of Compound 2, or a tautomer, isotopolog, or pharmaceutically acceptable salt thereof. In one embodiment, the method further comprises administering to the subject a therapeutically effective amount of rituximab.

In one embodiment, provided herein is a method of treating relapsed or refractory DLBCL, which comprises administering to a subject in need thereof a therapeutically effective amount of Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of preventing relapsed or refractory DLBCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In another embodiment, provided herein is a method of managing relapsed or refractory DLBCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of treating relapsed or refractory FL, which comprises administering to a subject in need thereof a therapeutically effective amount of Compound 1, or a tautomer, isotopolog, or pharmaceutically acceptable salt thereof. In one embodiment, the method further comprises administering to the subject a therapeutically effective amount of rituximab.

In one embodiment, provided herein is a method of treating relapsed or refractory FL, which comprises administering to a subject in need thereof a therapeutically effective amount of Compound 2, or a tautomer, isotopolog, or pharmaceutically acceptable salt thereof. In one embodiment, the method further comprises administering to the subject a therapeutically effective amount of rituximab.

In one embodiment, provided herein is a method of treating relapsed or refractory FL, which comprises administering to a subject in need thereof a therapeutically effective amount of Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of preventing relapsed or refractory FL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In another embodiment, provided herein is a method of managing relapsed or refractory FL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of treating relapsed or refractory MCL, which comprises administering to a subject in need thereof a therapeutically effective amount of Compound 1, or a tautomer, isotopolog, or pharmaceutically acceptable salt thereof. In one embodiment, the method further comprises administering to the subject a therapeutically effective amount of rituximab.

In one embodiment, provided herein is a method of treating relapsed or refractory MCL, which comprises administering to a subject in need thereof a therapeutically effective amount of Compound 2, or a tautomer, isotopolog, or pharmaceutically acceptable salt thereof. In one embodiment, the method further comprises administering to the subject a therapeutically effective amount of rituximab.

In one embodiment, provided herein is a method of treating relapsed or refractory MCL, which comprises administering to a subject in need thereof a therapeutically effective amount of Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of preventing relapsed or refractory MCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In another embodiment, provided herein is a method of managing relapsed or refractory MCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of treating relapsed or refractory PCNSL, which comprises administering to a subject in need thereof a therapeutically effective amount of Compound 1, or a tautomer, isotopolog, or pharmaceutically acceptable salt thereof. In one embodiment, the method further comprises administering to the subject a therapeutically effective amount of rituximab.

In one embodiment, provided herein is a method of treating relapsed or refractory PCNSL, which comprises administering to a subject in need thereof a therapeutically effective amount of Compound 2, or a tautomer, isotopolog, or pharmaceutically acceptable salt thereof. In one embodiment, the method further comprises administering to the subject a therapeutically effective amount of rituximab.

In one embodiment, provided herein is a method of treating relapsed or refractory PCNSL, which comprises administering to a subject in need thereof a therapeutically effective amount of Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In one embodiment, provided herein is a method of preventing relapsed or refractory PCNSL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In another embodiment, provided herein is a method of managing relapsed or refractory PCNSL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of rituximab.

In another embodiment, provided herein are methods for achieving a complete response, partial response, or stable disease, as determined by the Lugano response criteria in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having NHL. In another embodiment, provided herein are methods for achieving an increase in overall survival, progression-free survival, event-free survival, time to progression, or disease-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having NHL. In another embodiment, provided herein are methods for achieving an increase in overall survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having NHL. In another embodiment, provided herein are methods for achieving an increase in progression-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having NHL. In another embodiment, provided herein are methods for achieving an increase in event-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having NHL. In another embodiment, provided herein are methods for achieving an increase in time to progression in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having NHL. In another embodiment, provided herein are methods for achieving an increase in disease-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having NHL. In one embodiment, the methods further comprise administering to the subject a therapeutically effective amount of rituximab.

Pharmaceutical Compositions and Routes of Administration

The compound provided herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the compounds in the pharmaceutical composition may be at a level that will exercise the desired effect; about 0.001 mg/kg of a subject's body weight to about 1 mg/kg of a subject's body weight in unit dosage for both oral and parenteral administration.

A compound provided herein can be administered orally. In one embodiment, when administered orally, a compound provided herein is administered with a meal and water. In another embodiment, the compound provided herein is dispersed in water or juice (e.g., apple juice or orange juice) and administered orally as a solution or a suspension.

The compound provided herein can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a compound provided herein without an additional carrier, excipient or vehicle. In another embodiment, provided herein are compositions comprising an effective amount of a compound provided herein and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts. In general, all of the compositions are prepared according to known methods in pharmaceutical chemistry. Capsules can be prepared by mixing a compound provided herein with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a compound provided herein as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the compound provided herein can be delayed or prolonged by proper formulation. For example, a slowly soluble pellet of the compound provided herein can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound provided herein in oily or emulsified vehicles that allow it to disperse slowly in the serum.

The methods provided herein encompass treating a patient regardless of patient's age. In some embodiments, the subject is 18 years or older. In other embodiments, the subject is more than 18, 25, 35, 40, 45, 50, 55, 60, 65, or 70 years old. In other embodiments, the subject is less than 65 years old. In other embodiments, the subject is more than 65 years old.

Depending on the state of the disease to be treated and the subject's condition, Compound 1, Compound 2 or Compound 3 provided herein, or an enantiomer, mixture of enantiomers, tautomer, isotopolog, or pharmaceutically acceptable salt thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Compound 1, Compound 2 or Compound 3 provided herein, or an enantiomer, mixture of enantiomers, tautomer, isotopolog, or pharmaceutically acceptable salt thereof, may be formulated, alone or together, in suitable dosage unit with pharmaceutically acceptable excipients, carriers, adjuvants and vehicles, appropriate for each route of administration.

In one embodiment, Compound 1, Compound 2 or Compound 3 provided herein, or an enantiomer, mixture of enantiomers, tautomer, isotopolog, or pharmaceutically acceptable salt thereof, is administered orally. In another embodiment, the compound of Compound 1, Compound 2 or Compound 3 provided herein, or an enantiomer, mixture of enantiomers, tautomer, isotopolog, or pharmaceutically acceptable salt thereof, is administered parenterally. In yet another embodiment, the compound of Compound 1, Compound 2 or Compound 3 provided herein, or an enantiomer, mixture of enantiomers, tautomer, isotopolog, or pharmaceutically acceptable salt thereof, is administered intravenously.

Compound 1, Compound 2 or Compound 3 provided herein, or an enantiomer, mixture of enantiomers, tautomer, isotopolog, or pharmaceutically acceptable salt thereof, can be delivered as a single dose such as, e.g., a single bolus injection, or oral capsules, tablets or pills; or over time, such as, e.g., continuous infusion over time or divided bolus doses over time. The compounds as described herein can be administered repeatedly if necessary, for example, until the patient experiences stable disease or regression, or until the patient experiences disease progression or unacceptable toxicity.

Compound 1, Compound 2 or Compound 3 provided herein, or an enantiomer, mixture of enantiomers, tautomer, isotopolog, or pharmaceutically acceptable salt thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered once or more than once each day, for example, for a period of time. The term "continuous" is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered daily for an uninterrupted period of at least 7 days to 52 weeks. The term "intermittent" or "intermittently" as used herein is intended to mean stopping and starting at either regular or irregular intervals. For example, intermittent administration of Compound 1, Compound 2 or Compound 3 provided herein, or an enantiomer, mixture of enantiomers, tautomer, isotopolog, or pharmaceutically acceptable salt thereof, is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, Compound 1, Compound 2 or Compound 3 provided herein, or an enantiomer, mixture of enantiomers, tautomer, isotopolog, or pharmaceutically acceptable salt thereof, is administered once a day. In another embodiment, Compound 1, Compound 2 or Compound 3 provided herein, or an enantiomer, mixture of enantiomers, tautomer, isotopolog, or pharmaceutically acceptable salt thereof, is administered twice a day. In yet another embodiment, Compound 1, Compound 2 or Compound 3 provided herein, or an enantiomer, mixture of enantiomers, tautomer, isotopolog, or pharmaceutically acceptable salt thereof, is administered three times a day. In still another embodiment, Compound 1, Compound 2 or Compound 3 provided herein, or an enantiomer, mixture of enantiomers, tautomer, isotopolog, or pharmaceutically acceptable salt thereof, is administered four times a day.

In certain embodiments, the methods provided herein include an administration of a therapeutically effective amount of Compound 1, Compound 2 or Compound 3 in one or more 7-day treatment cycles. In another embodiment, the methods provided herein include an administration of a therapeutically effective amount of Compound 1, Compound 2 or Compound 3 on days 1 to 5 of a 7-day cycle.

In certain embodiments, the methods provided herein include an administration of a therapeutically effective amount of Compound 1, Compound 2 or Compound 3 in one or more 14-day treatment cycles. In another embodiment, the methods provided herein include an administration of a therapeutically effective amount of Compound 1, Compound 2 or Compound 3 on days 1 to 5 of a 14-day cycle. In another embodiment, the methods provided herein include an administration of a therapeutically effective amount of Compound 1, Compound 2 or Compound 3 on days 1 to 7 of a 14-day cycle. In another embodiment, the methods provided herein include an administration of a therapeutically effective amount of Compound 1, Compound 2 or Compound 3 on days 1 to 10 of a 14-day cycle.

In one embodiment, the methods provided herein include an administration of a therapeutically effective amount of Compound 1, Compound 2 or Compound 3 in one or more 28-day treatment cycles. In another embodiment, the methods provided herein include an administration of a therapeutically effective amount of Compound 1, Compound 2 or Compound 3 on days 1 to 14 of a 28-day cycle. In another embodiment, the methods provided herein include an administration of a therapeutically effective amount of Compound 1, Compound 2 or Compound 3 on days 1 to 21 of a 28-day cycle. In another embodiment, the methods provided herein include an administration of a therapeutically effective amount of Compound 1, Compound 2 or Compound 3 on days 1 to 5, days 8 to 12, days 15 to 19, and days 22 to 26 of a 28-day cycle. In another embodiment, the methods provided herein include an administration of a therapeutically effective amount of Compound 1, Compound 2 or Compound 3 on days 1 to 5 and days 15 to 19 of a 28-day cycle. In another embodiment, the methods provided herein include an administration of a therapeutically effective amount of Compound 1, Compound 2 or Compound 3 on days 1 to 7 and days 15 to 21 of a 28-day cycle. In another embodiment, the methods provided herein include an administration of a therapeutically effective amount of Compound 1, Compound 2 or Compound 3 on days 1 to 10 and days 15 to 24 of a 28-day cycle.

In one embodiment, Compound 1, Compound 2 or Compound 3 is administered once daily for 5 days followed by 2 days of rest. In one embodiment, Compound 1, Compound 2 or Compound 3 is administered once daily for 5 days followed by 9 days of rest. In one embodiment, Compound 1, Compound 2 or Compound 3 is administered once daily for 7 days followed by 7 days of rest. In one embodiment, Compound 1, Compound 2 or Compound 3 is administered once daily for 10 days followed by 4 days of rest. In one embodiment, Compound 1, Compound 2 or Compound 3 is administered once daily for 14 days followed by 14 days of rest. In one embodiment, Compound 1, Compound 2 or Compound 3 is administered once daily for 21 days followed by 7 days of rest.

In certain embodiments, the treatment includes an administration of a therapeutically effective amount of rituximab in one or more treatment cycles. In one embodiment, rituximab is administered once every 7 days. In one embodiment, rituximab is administered once every 4 weeks. In one embodiment, rituximab is administered once every 8 weeks. In one embodiment, rituximab is administered at days 1, 8, 15, and 22 of the first 28-day cycle, administered at day 1 of the second to the sixth 28-day cycles, and then administered once every 8 weeks.

In one embodiment, the method provided herein comprises (i) administering rituximab on days 1, 8, 15, and 22 of the first 28-day cycle ("Cycle 1"), on day 1 of the second to the sixth 28-day cycles, and then once every 8 weeks; and (ii) administering Compound 1 in cycles of once daily for 5 days followed by 2 days of rest, starting on day 1 of Cycle 1.

In one embodiment, the method provided herein comprises (i) administering rituximab on days 1, 8, 15, and 22 of the first 28-day cycle ("Cycle 1"), on day 1 of the second to the sixth 28-day cycles, and then once every 8 weeks; and (ii) administering Compound 1 in cycles of once daily for 5 days followed by 9 days of rest, starting on day 1 of Cycle 1.

In one embodiment, the method provided herein comprises (i) administering rituximab on days 1, 8, 15, and 22 of the first 28-day cycle ("Cycle 1"), on day 1 of the second to the sixth 28-day cycles, and then once every 8 weeks; and (ii) administering Compound 1 in cycles of once daily for 7 days followed by 7 days of rest, starting on day 1 of Cycle 1.

In one embodiment, the method provided herein comprises (i) administering rituximab on days 1, 8, 15, and 22 of the first 28-day cycle ("Cycle 1"), on day 1 of the second to the sixth 28-day cycles, and then once every 8 weeks; and (ii) administering Compound 1 in cycles of once daily for 10 days followed by 4 days of rest, starting on day 1 of Cycle 1.

In one embodiment, the method provided herein comprises (i) administering rituximab on days 1, 8, 15, and 22 of the first 28-day cycle ("Cycle 1"), on day 1 of the second to the sixth 28-day cycles, and then once every 8 weeks; and (ii) administering Compound 1 in cycles of once daily for 14 days followed by 14 days of rest, starting on day 1 of Cycle 1.

In one embodiment, the method provided herein comprises (i) administering rituximab on days 1, 8, 15, and 22 of the first 28-day cycle ("Cycle 1"), on day 1 of the second to the sixth 28-day cycles, and then once every 8 weeks; and (ii) administering Compound 1 in cycles of once daily for 21 days followed by 7 days of rest, starting on day 1 of Cycle 1.

Any treatment cycle described herein can be repeated for at least 1, 2, 3, 4, 5, 6, 7, 8, or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In some embodiments, a therapeutically effective amount of Compound 1, Compound 2 or Compound 3, and/or rituximab is administered for 1 to 13 cycles of 28 days (e.g., about 1 year). In certain instances, the cycling therapy is not limited to the number of cycles, and the therapy is continued until disease progression. Cycles can in certain instances include varying the duration of administration periods and/or rest periods described herein.

EXAMPLES

The following Examples are presented by way of illustration, not limitation. Compounds are named using the automatic name generating tool provided in ChemBiodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.

Abbreviations Used

| | |
|---|---|
| DCM | Dichloromethane |
| DIEA | N,N-Diisopropylethylamine |
| DMF | N,N-Dimethylformamide |
| DMSO | Dimethylsulfoxide |
| ESI | Electrospray ionization |
| EtOAc | Ethyl acetate |
| LCMS | Liquid chromatography mass spectrometry |
| MeOH | Methanol |
| MS | Mass spectrometry |
| NMP | N-Methylpyrrolidone |
| NMR | Nuclear magnetic resonance |
| THF | Tetrahydrofuran |

Example 1: Synthesis of (S)-2-(2,6-Dioxopiperidin-3-yl)-4-((2-fluoro-4-((3-morpholinoazetidin-1-yl)methyl)benzyl)amino)isoindoline-1,3-dione (Compound 1)

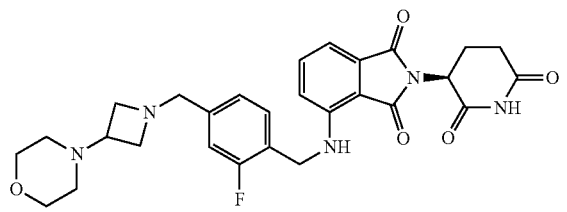 [SMILES: O=C1CC[C@H](N2C(=O)c3cccc(NCc4ccc(CN5CC(N6CCOCC6)C5)cc4F)c3C2=O)C(=O)N1]

(S)-2-(2,6-Dioxopiperidin-3-yl)-4-((2-fluoro-4-(hydroxymethyl)benzyl)amino)isoindoline-1,3-dione A suspension of (S)-4-amino-2-(2,6-dioxopiperidin-3-yl)isoindoline-1,3-dione (5.00 g, 18.3 mmol) and 2-fluoro-4-(hydroxymethyl)benzaldehyde (2.82 g, 18.30 mmol) in 2:1 dioxane-MeOH (75 mL) was cooled to 0° C. and $B_{10}H_{14}$ (4.92 g, 40.3 mmol) was added in small portions over 5 minutes. The reaction flask was fitted with a septum and needle vent (pressure) and vigorously stirred for 10 minutes. The mixture was allowed to reach ambient temperature and stirred for 3 hours. The mixture was concentrated and the residue purified by silica gel chromatography (0-10% MeOH-DCM) to provide (S)-2-(2,6-dioxopiperidin-3-yl)-4-((2-fluoro-4-(hydroxymethyl)benzyl)amino)isoindoline-1,3-dione as a yellow solid (4.23 g, 56%). LCMS (ESI) m/z 411.8 [M+H]$^+$.

(S)-4-((4-(Chloromethyl)-2-fluorobenzyl)amino)-2-(2,6-dioxopiperidin-3-yl)isoindoline-1,3-dione A solution of (S)-2-(2,6-dioxopiperidin-3-yl)-4-((2-fluoro-4-(hydroxymethyl)benzyl)amino)isoindoline-1,3-dione (0.727 g, 1.77 mmol) in dry NMP (6 mL) was cooled to 0° C. and methane sulfonyl chloride (0.275 mL, 3.35 mmol) and DIEA (0.617 mL, 3.53 mmol) were added sequentially. The reaction mixture was allowed to reach ambient temperature and was stirred for 18 hours. The reaction mixture was slowly added to $H_2O$ (60 mL) cooled to 0° C. with vigorous mixing. The resulting suspension was filtered and the collected solid was washed with $H_2O$ and $Et_2O$. The solid was dissolved in EtOAc and the solution dried with $MgSO_4$, filtered and concentrated to provide (S)-4-((4-(chloromethyl)-2-fluorobenzyl)amino)-2-(2,6-dioxopiperidin-3-yl)isoindoline-1,3-dione as a yellow solid (0.600 g, 79%). LCMS (ESI) m/z 430.0 [M+H]$^+$.

(S)-2-(2,6-Dioxopiperidin-3-yl)-4-((2-fluoro-4-((3-morpholinoazetidin-1-yl)methyl)benzyl)amino)isoindoline-1,3-dione To a solution of (S)-4-((4-(chloromethyl)-2-fluorobenzyl)amino)-2-(2,6-dioxopiperidin-3-yl)isoindoline-1,3-dione (300 mg, 0.698 mmol) in dry DMSO (1.0 mL) was added 4-(azetidin-3-yl)morpholine hydrochloride (125 mg, 0.698 mmol) and DIEA (0.122 mL, 0.698 mmol). The reaction mixture was stirred at ambient temperature for 18 hours and was diluted with DMSO (1 mL). The solution was purified by chiral reverse-phase chromatography to give (S)-2-(2,6-dioxopiperidin-3-yl)-4-((2-fluoro-4-((3-morpholinoazetidin-1-yl)methyl)benzyl)amino)isoindoline-1,3-dione (89 mg, 24%, 97% ee). LCMS (ESI) m/z 536.2 [M+H]$^+$.

Example 2: Synthesis of (R)-2-(2,6-Dioxopiperidin-3-yl)-4-((2-fluoro-4-((3-morpholinoazetidin-1-yl)methyl)benzyl)amino)isoindoline-1,3-dione (Compound 2)

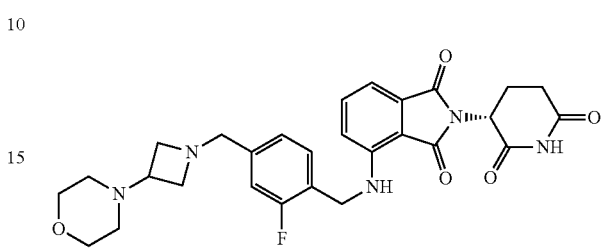

The chiral reverse-phase chromatography described in Example 1 additionally provided (R)-2-(2,6-dioxopiperidin-3-yl)-4-((2-fluoro-4-((3-morpholinoazetidin-1-yl)methyl)benzyl)amino)isoindoline-1,3-dione (16 mg, 97% ee). LCMS (ESI) m/z 535.6 [M+H]$^+$.

Example 3: Synthesis of 2-(2,6-Dioxopiperidin-3-yl)-4-((2-fluoro-4-((3-morpholinoazetidin-1-yl)methyl)benzyl)amino)isoindoline-1,3-dione (Compound 3)

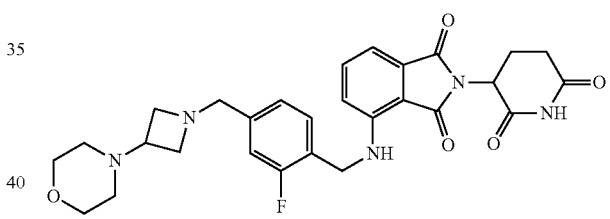

(4-Bromo-3-fluoro-phenyl)methanol

A solution of 4-bromo-3-fluoro-benzoic acid (15.0 g, 68.5 mmol) in THF (150 mL) was cooled to 0° C. and borane-dimethyl sulfide complex (13.7 mL, 137 mmol, 10 M in THF) was added dropwise under nitrogen atmosphere. The cooling bath was removed and the mixture was stirred at ambient temperature for 12 hours. The mixture was cooled to 0° C., quenched with MeOH (50 mL) and poured into water (30 mL). The mixture was concentrated under vacuum and the residual aqueous mixture was diluted with ethyl acetate (150 mL) and water (150 mL) and stirred for 15 minutes. The organic phase was removed and the aqueous phase was extracted with ethyl acetate (150 mL×2). The organic fractions were combined, dried with anhydrous sodium sulfate, filtered, and concentrated under vacuum. The residue was purified by silica gel column chromatography (2-10% ethyl acetate in petroleum ether) to give (4-bromo-3-fluoro-phenyl)methanol (13.1 g, 93.3% yield) as a colorless liquid. LCMS (ESI) m/z 187.0 [MH-18$^+$]. $^1$H NMR (400 MHz, CDCl$_3$) δ ppm 7.54-7.45 (m, 1H), 7.14 (d, J=9.2 Hz, 1H), 7.00 (d, J=7.9 Hz, 1H), 4.64 (d, J=4.6 Hz, 2H), 2.20 (br s, 1H).

(4-Bromo-3-fluoro-phenyl)methoxy-tert-butyl-dimethyl-silane

A solution of (4-bromo-3-fluoro-phenyl)methanol (13.1 g, 63.9 mmol) and imidazole (12.2 g, 179 mmol) in DMF (150 mL) was cooled to 0° C. and tert-butylchlorodimethylsilane (14.4 g, 95.8 mmol) was added. The cooling bath was removed and the mixture was stirred at ambient temperature for 16 hours. The reaction was poured into chilled water (30 mL), diluted with ethyl acetate (100 mL) and water (100 mL) and stirred for 15 minutes. The organic phase was removed and the aqueous phase was extracted with ethyl acetate (150 mL×2). The organic fractions were combined, washed with saturated NaCl (50 mL×2), dried with anhydrous sodium sulfate, filtered and concentrated under vacuum. The residue was purified by silica gel column chromatography (0-10% ethyl acetate in petroleum ether) to give (4-bromo-3-fluoro-phenyl)methoxy-tert-butyl-dimethyl-silane (18.6 g, 91.2% yield) as a colorless liquid. $^1$H NMR (400 MHz, CDCl$_3$) δ ppm 7.49 (dd, J=7.1, 8.1 Hz, 1H), 7.18-7.08 (m, 1H), 7.01-6.92 (m, 1H), 4.69 (s, 2H), 0.96 (s, 9H), 0.12 (s, 6H).

4-[[tert-Butyl(dimethyl)silyl]oxymethyl]-2-fluoro-benzaldehyde

Under an atmosphere of nitrogen a solution of (4-bromo-3-fluoro-phenyl)methoxy-tert-butyl-dimethyl-silane (18.6 g, 58.3 mmol) in THF (150 mL) was cooled to −78° C. and n-BuLi (25.6 mL, 64.0 mmol, 2.5 M in hexane) was added dropwise. The mixture was stirred at −78° C. for 5 minutes and DMF (5.83 mL, 75.7 mmol) was added. The mixture was stirred at −78° C. for 2 hours and allowed to warm to ambient temperature. The reaction mixture was cooled to 0° C. and quenched with saturated ammonium chloride (60 mL) and water (30 mL). The mixture was extracted with ethyl acetate (2×150 mL) and the combined extracts were dried over sodium sulfate, filtered and concentrated. The residue was purified by silica gel column chromatography (0-2% ethyl acetate in petroleum ether) to give 4-[[tert-butyl(dimethyl)silyl]oxymethyl]-2-fluoro-benzaldehyde (11.5 g, 73.5% yield) as a yellow liquid. MS (ESI) m/z: 269.1 [M+1]$^+$.

3-((4-(((tert-Butyldimethylsilyl)oxy)methyl)-2-fluorobenzyl)amino)phthalic Acid A solution of 4-[[tert-butyl(dimethyl)silyl]oxymethyl]-2-fluoro-benzaldehyde (7.50 g, 27.9 mmol) and 3-aminophthalic acid (5.06 g, 27.9 mmol) in 1:10 acetic acid-MeOH (110 mL) was stirred at 25° C. for 30 minutes and was cooled to 0° C. Borane 2-methylpyridine complex (4.48 g, 41.9 mmol) was added and the mixture was allowed to reach ambient temperature. The mixture was stirred at ambient temperature for 16 hours and the mixture was concentrated under reduced pressure. The residue was diluted with water (25 mL) and ethyl acetate (25 mL) and stirred for 15 minutes. The organic layer was removed and the aqueous layer was extracted with ethyl acetate (30 mL×2). The organic fractions were combined, dried with anhydrous sodium sulfate, filtered, and concentrated. The residue was purified by silica gel column chromatography (2-5% ethyl acetate in petroleum ether) to give 3-((4-(((tert-butyldimethylsilyl)oxy)methyl)-2-fluorobenzyl)amino)phthalic acid (9.90 g, 81.8% yield) as a white solid. LCMS (ESI) m/z: 434.1 [M+1]$^+$.

4-((4-(((tert-Butyldimethylsilyl)oxy)methyl)-2-fluorobenzyl)amino)-2-(2,6-dioxopiperidin-3-yl)isoindoline-1,3-dione A solution of 3-((4-(((tert-butyldimethylsilyl)oxy)methyl)-2-fluorobenzyl)amino)phthalic acid (11.8 g, 27.2 mmol) and 3-aminopiperidine-2,6-dione hydrochloride (6.72 g, 40.8 mmol) in pyridine (150 mL) was stirred at 120° C. for 12 hours under a nitrogen atmosphere. The mixture was concentrated under reduced pressure and the residue was purified by silica gel column chromatography (2-5% ethyl acetate in petroleum ether) to give 4-((4-(((tert-butyldimethylsilyl)oxy)methyl)-2-fluorobenzyl)amino)-2-(2,6-dioxopiperidin-3-yl)isoindoline-1,3-dione (9.90 g, 69.2% yield) as a yellow solid. LCMS (ESI) m/z: 526.2 [M+1]$^+$.

2-(2,6-Dioxopiperidin-3-yl)-4-((2-fluoro-4-(hydroxymethyl)benzyl)amino)isoindoline-1,3-dione To a solution of 4-((4-(((tert-butyldimethylsilyl)oxy)methyl)-2-fluorobenzyl)amino)-2-(2,6-dioxopiperidin-3-yl)isoindoline-1,3-dione (9.90 g, 18.8 mmol) in THF (100 mL) was added concentrated sulfuric acid (20.0 mL, 368 mmol) and the mixture was stirred at ambient temperature for 12 hours. The mixture was concentrated under vacuum and the residue was treated with 1:5 ethyl acetate-petroleum ether (20 mL). The resulting suspension was stirred for 30 minutes and filtered. The collected solid was washed with 1:5 ethyl acetate-petroleum ether and dried in vacuum to give 2-(2,6-dioxopiperidin-3-yl)-4-((2-fluoro-4-(hydroxymethyl)benzyl)amino)isoindoline-1,3-dione (6.58 g, 85.2% yield) as a yellow solid. MS (ESI) m/z: 412.0 [M+1]$^+$. $^1$H NMR (400 MHz, DMSO-d$_6$) δ ppm 11.12 (s, 1H), 7.54 (dd, J=7.3, 8.4 Hz, 1H), 7.33 (t, J=7.8 Hz, 1H), 7.16-7.07 (m, 3H), 7.05 (d, J=7.0 Hz, 1H), 6.99 (d, J=8.5 Hz, 1H), 5.33-5.25 (m, 1H), 5.07 (dd, J=5.3, 12.9 Hz, 1H), 4.59 (d, J=6.3 Hz, 2H), 4.47 (d, J=5.8 Hz, 2H), 2.95-2.84 (m, 1H), 2.65-2.52 (m, 2H), 2.09-2.01 (m, 1H).

4-((4-(chloromethyl)-2-fluorobenzyl)amino)-2-(2,6-dioxopiperidin-3-yl)isoindoline-1,3-dione A solution of 2-(2,6-dioxopiperidin-3-yl)-4-((2-fluoro-4-(hydroxymethyl)benzyl)amino)isoindoline-1,3-dione (6.58 g, 16.0 mmol) in dichloromethane (200 mL) was cooled to 0° C. and thionyl chloride (20.0 mL, 276 mmol) was added dropwise. After complete addition, the cooling bath was removed and the reaction mixture was stirred at ambient temperature for 2 hours. The mixture was concentrated under vacuum and the residue was purified by silica gel column chromatography (1.00-1.25% MeOH in dichloromethane) to give 4-((4-(chloromethyl)-2-fluorobenzyl)amino)-2-(2,6-dioxopiperidin-3-yl)isoindoline-1,3-dione (3.80 g, 55.4% yield) as a yellow solid. LCMS (ESI) m/z: 430.0 [M+1]$^+$. $^1$H NMR (400 MHz, DMSO-d$_6$) δ ppm 11.12 (s, 1H), 7.54 (dd, J=7.3, 8.4 Hz, 1H), 7.38 (t, J=7.9 Hz, 1H), 7.32 (dd, J=1.5, 11.0 Hz, 1H), 7.24 (dd, J=1.6, 7.8 Hz, 1H), 7.16 (t, J=6.3 Hz, 1H), 7.06 (d, J=6.9 Hz, 1H), 6.98 (d, J=8.5 Hz, 1H), 5.08 (dd, J=5.3, 12.9 Hz, 1H), 4.74 (s, 2H), 4.63 (d, J=6.3 Hz, 2H), 2.95-2.85 (m, 1H), 2.66-2.53 (m, 2H), 2.09-2.02 (m, 1H).

2-(2,6-Dioxopiperidin-3-yl)-4-((2-fluoro-4-((3-morpholinoazetidin-1-yl)methyl)benzyl)amino)isoindoline-1,3-dione To a solution of 4-((4-(chloromethyl)-2-fluorobenzyl)amino)-2-(2,6-dioxopiperidin-3-yl)isoindoline-1,3-dione (215 mg, 0.500 mmol) (prepared as described herein) and 4-(azetidin-3-yl)morpholine hydrochloride (107 mg, 0.600 mmol) in dry DMSO (1.7 mL) was added DIEA (262 µL, 1.50 mmol) and the mixture stirred at ambient temperature for 48 hours. The reaction mixture was diluted with 20% formic acid in DMSO (2.5 mL) and filtered through a membrane syringe filter (0.45 m nylon). The solution was purified using standard methods to provide 2-(2,6-dioxopiperidin-3-yl)-4-((2-fluoro-4-((3-morpholinoazetidin-1-yl)methyl)benzyl)amino)isoindoline-1,3-dione (173 mg, 64.6% yield). LCMS (ESI) m/z 536.2 [M+H]$^+$.

Example 4: Cell-Based Assays Using Compounds as Single Agents

The following are examples of cell-based assays that can be used to determine the anti-proliferative activity and apoptotic effect of compounds described herein using exemplary non-Hodgkin lymphoma (NHL) cell lines.

Cell Proliferation and Viability Assay Using SU-DHL-4 Cell Line:

The following exemplary assay uses a DLBCL cell line, for example, the SU-DHL-4 cell line (Deutsche Sammlung von Mikroorganismen und Zellkulturen GmbH [DSMZ]: catalogue number ACC-495) at 120 hours post-treatment. The seeding density for SU-DHL-4 can be optimized to ensure assay linearity in 1536-well plates.

Increasing concentrations (0.5 nM to 10 M) of Compounds 1, 2, and 3 were each spotted in a 20-point dilution fashion (unevenly spaced data points) via an acoustic dispenser (EDC ATS-100) into an empty 1536-well plate. The DMSO concentration was kept constant for a final assay concentration of 0.1% DMSO. Prior to testing, SU-DHL-4 cells were grown in RPMI-1640 (Roswell Park Memorial Institute-1640) medium with 10% FBS (fetal bovine serum: HyClone) and expanded in culture flasks to provide sufficient amounts of starting material. Cells were then diluted to 500 cells per well in a 5 µL volume, and added directly to the compound-spotted 1536-well plates. Cells were allowed to grow for 120 hours in 5% $CO_2$ at 37° C. At the time when exposure of cells to compound began ($t_0$), initial viable cell number was assessed via Cell Titer-Glo® Luminescent Cell Viability Assay at a 1 vol: 2 vol ratio according to manufacturer's instructions (Promega Corporation, Madison, Wis.) by quantifying the level of luminescence generated by adenosine-5'-triphosphate (ATP) present in viable cells. After 120 hours, cell viability of the treated cells was assessed via Cell Titer-Glo© and read for luminescence. All growth inhibition curves were processed and evaluated using Activity Base (IDBS, Alameda, Calif.). Cell viability $IC_{50}$ values were calculated using a four parameter logistic model (sigmoidal dose-response model):

$$y=(A+((B-A)/(1+((C/x)^D))))$$

wherein:
$A=Y_{Min}$
$B=Y_{Max}$
$C=EC_{50}$
D=Hill slope
$IC_{50}$=the concentration of the compound when Y=50% of DMSO control
Y=cell viability measured as luminescence unit, and
x=concentration of compound.

Compounds 1, 2 and 3 were found to have activity in SU-DHL-4 cell proliferation assay (Table 4).

TABLE 4

Antiproliferative Activity of Compounds 1, 2, and 3 in SU-DHL-4 Cell Line.

| Cpd # | Cpd Structure | Cpd Name | IC50 |
|---|---|---|---|
| 1 | | (S)-2-(2,6-dioxopiperidin-3-yl)-4-(2-fluoro-4-((3-morpholinoazetidin-1-yl)methyl)benzylamino)isoindoline-1,3-dione | <0.2 µM |
| 2 | | (R)-2-(2,6-dioxopiperidin-3-yl)-4-(2-fluoro-4-((3-morpholinoazetidin-1-yl)methyl)benzylamino)isoindoline-1,3-dione | <0.2 µM |

TABLE 4-continued

Antiproliferative Activity of Compounds 1, 2, and 3 in SU-DHL-4 Cell Line.

| Cpd # | Cpd Structure | Cpd Name | IC50 |
|---|---|---|---|
| 3 | | 2-(2,6-dioxopiperidin-3-yl)-4-(2-fluoro-4-((3-morpholinoazetidin-1-yl)methyl)benzylamino)isoindoline-1,3-dione | <0.2 µM |

Cell Proliferation and Viability Assay Using NHL Cell Lines:

The following exemplary anti-proliferative assay uses exemplary non-Hodgkin lymphoma (NIL) cell lines (including diffuse large B-cell lymphoma (DLBCL), follicular lymphoma (FL), and mantle cell lymphoma (MCL)) (Table 5). The in vitro growth inhibitory activity of Compound 1 described herein was evaluated using a 384-well flow cytometry assay.

TABLE 5

NHL Cell Lines.

| Cell Line | Tumor type | Tumor subtype | Culture conditions |
|---|---|---|---|
| ULA | DLBCL | not specified | RPMI + 10% FBS, 1X NEAA, 2 mM L-glutamine |
| SU-DHL-5 | DLBCL | not specified | |
| OCI-LY18 | DLBCL | not specified | |
| TMD8 | DLBCL | ABC | |
| SU-DHL-2 | DLBCL | ABC | |
| Farage | DLBCL | PMBL, | |
| SU-DHL-10 | DLBCL | GCB | |
| NU-DHL-1 | DLBCL | GCB | |
| VAL | DLBCL | not specified | |
| WILL-2 | DLBCL | not specified | |
| SU-DHL-6 | DLBCL | GCB | |
| KARPAS-422 | DLBCL | GCB | |
| NU-DUL-1 | DLBCL | ABC | |
| KARPAS-1106P | DLBCL | PMBL | |
| OCI-LY1 | DLBCL | GCB | |
| SU-DHL-1 | DLBCL | not specified | |
| WSU-DLCL2 | DLBCL | GCB | |
| STR428 | DLBCL | not specified | |
| U-2946 | DLBCL | not specified | |
| U-2940 | DLBCL | PMBL | |
| OCI-LY-19 | DLBCL | GCB | |
| CARNAVAL | DLBCL | not specified | |
| Toledo | DLBCL | GCB | |
| RC-K8 | DLBCL | ABC | |
| SU-DHL-8 | DLBCL | GCB | |
| OCI-LY10 | DLBCL | ABC | |
| SU-DHL-16 | DLBCL | GCB | |
| U-2932 | DLBCL | ABC | |
| WILL-1 | DLBCL | not specified | |
| SU-DHL-4 | DLBCL | GCB | |
| Pfeiffer | DLBCL | GCB | |
| U-2904 | DLBCL | not specified | |
| WSU-DLCL | DLBCL | GCB | |
| HT | DLBCL | GCB | |
| RIVA | DLBCL | ABC | |
| ROS-50 | DLBCL | not specified | |
| GCBDB | DLBCL | GCB | |
| OCI-LY-7 | DLBCL | GCB | IMDM + 20% Human Plasma |
| OCI-LY-3 | DLBCL | ABC | |
| DOHH2 | FL | not specified | RPMI + 10% FBS, 1X NEAA, |

TABLE 5-continued

NHL Cell Lines.

| Cell Line | Tumor type | Tumor subtype | Culture conditions |
|---|---|---|---|
| RL | FL | not specified | 2 mM L-glutamine |
| Mino | MCL | not specified | RPMI1640 + 15% FBS + 2 mM L-glutamine + 10 mM Hepes + 1 mM sodium pyruvate + 4.5 g/L glucose |
| Rec-1 | MCL | not specified | RPMI + 10% FBS + 2 mM L-glutamine |

ABC = activated B-cell like;
FBS = fetal bovine serum;
GCB = germinal center B-cell;
IMDM = Iscove's Modified Dulbecco's medium;
NEAA = non-essential amino acid;
RPMI = RPMI1640.

The cell lines in Table 5 were plated in 384-well flat bottom plates and assessed with increasing concentrations of compound ranging from 0.00015 to 10 µM or dimethyl sulfoxide (DMSO) control. The final concentration of DMSO was 0.1% (v/v). Following the addition of Compound 1 or DMSO and incubation for 120 hours, cell number and cell death were analyzed by flow cytometry (Attune®, Thermo Fisher) using Annexin V and the live-cell impermeant DNA dye, DRAQ7. Phosphatidylserine translocates from the inner layer to the outer layer of the cell membrane early in apoptosis and Annexin V binds to the exposed phosphatidylserine found on the surface of an apoptotic cell. The vital dye DRAQ7 is excluded by intact live cells and only stains cells that have died as a result of apoptosis or necrosis.

Flow cytometry data analysis was then performed using the Flow Jo_v10 software to determine the number of viable cells (Annexin V and DRAQ7 double negative staining cells) and percentage of apoptotic cells (Annexin V positive cells) for each condition. The live cell count for every concentration was normalized to the DMSO control (considered as 100%) to calculate the percentage of viable cells remaining after treatment and graphed using GraphPad Prism 7.03. The $IC_{50}$ (50% inhibitory concentration) and $E_{max}$ (maximum efficacy achieved) values were then calculated by performing nonlinear regression curve fitting using log(inhibitor) vs. normalized response—variable slope analysis on GraphPad Prism 7.03. Area under the curve (AUC) was calculated by performing area under curve analysis on GraphPad Prism 7.03. Similarly, for apoptosis analysis, the percentage of apoptosis combining both "early"

(Annexin V positive and DRAQ7 negative) and "late" apoptosis (Annexin V and DRAQ7 positive) cell gates relative to DMSO was graphed using GraphPad Prism 7.03. The AUC, $EC_{50}$ (concentration of Compound 1 that produces half-maximal apoptosis response) and $Y_{max}$ (maximal percentage of apoptosis achieved) values from apoptosis curves were calculated by performing area under curve analysis and nonlinear regression curve fitting using log (agonist) vs. normalized response—Variable slope analysis on GraphPad Prism 7.03.

In Table 6, dose-response proliferation curves for the panel of NHL cell lines and non-linear curve-fit regression were used to determine $IC_{50}$, AUC, and $E_{max}$ for % viable cells ($E_{max}$ for viability varies between 100 at low doses and 0 at high doses, which corresponds to inhibition of all viable cells), and dose-response apoptosis curves were used to determine the $EC_{50}$, AUC, and $Y_{max}$ for % apoptosis ($Y_{max}$ for apoptosis varies from 0 at low doses and 100 at higher doses which corresponds to death of all cells). Tumor cells were exposed to serial dilutions (0.00015 to 10 μM) of Compound 1 or dimethyl sulfoxide (DMSO) control for 5 days. Viability and apoptosis for all cell lines was determined by Annexin V/7-aminoactinomycin D (7-AAD) flow cytometry. Compound 1 was found to have antiproliferative activity and apoptotic effect in NHL cell lines (Table 6).

TABLE 6

Antiproliferative Activity and Apoptotic Effect of Compound 1 in NHL Cell Lines.

| Cell Line | % Viable Cells | | | Apoptosis | | |
|---|---|---|---|---|---|---|
| | AUC | $IC_{50}$ | $E_{max}$ | AUC | $EC_{50}$ | $Y_{max}$ |
| ULA | 0.5518 | 0.00099 | 0.02523 | 995.3 | 0.00179 | 99.76 |
| SU-DHL-5 | 1.873 | 0.002389 | 0.1398 | 934.1 | 0.003603 | 95.23 |
| OCI-LY18 | 1.965 | 0.0009441 | 0.05973 | 965.2 | 0.002976 | 97.44 |
| TMD8 | 4.187 | 0.002459 | 0.245 | 963.3 | 0.006172 | 97.2 |
| SU-DHL-2 | 5.586 | 0.001263 | 0.2145 | 928.4 | 0.006242 | 95.98 |
| Farage | 10.16 | 0.002375 | 0.7936 | 728.7 | 0.03017 | 84.17 |
| SU-DHL-10 | 10.36 | 0.006101 | 0.6716 | 903 | 0.03942 | 92.27 |
| NU-DHL-1 | 12.37 | 0.001073 | 0.4919 | 981.8 | 0.001267 | 99.17 |
| VAL | 14.62 | 0.0005703 | 0.9632 | 936.7 | 0.0006045 | 95.68 |
| WILL-2 | 17.1 | 0.002359 | 0.03115 | 916.9 | 0.08971 | 99.43 |
| SU-DHL-6 | 19.94 | 0.03248 | 0.2469 | 920.7 | 0.1045 | 95.92 |
| KARPAS-422 | 19.97 | 0.01313 | 0.8721 | 911.9 | 0.0461 | 93.99 |
| NU-DUL-1 | 22.12 | 0.03527 | 0.0228 | 962.8 | 0.06304 | 99.84 |
| KARPAS-1106P | 22.22 | 0.01748 | 0.1698 | 885.2 | 0.09182 | 97.08 |
| OCI-LY1 | 22.77 | 0.006002 | 1.037 | 852.3 | 0.03338 | 90.09 |
| SU-DHL-1 | 31.14 | 0.0005495 | 2.485 | 690.1 | 0.001105 | 73.83 |
| WSU-DLCL2 | 36.7 | 0.01691 | 1.387 | 858.9 | 0.08473 | 92.1 |
| STR428 | 43.48 | 0.09471 | 1.227 | 905.9 | 0.1016 | 95.17 |
| U-2946 | 45.47 | 0.004604 | 0.4821 | 762.6 | 0.1922 | 93.34 |
| U-2940 | 70.43 | 0.006313 | 5.192 | 792.5 | 0.0314 | 82.19 |
| OCI-LY19 | 72.49 | 0.02944 | 3.228 | 706.2 | 0.2829 | 80.91 |
| CARNAVAL | 110.6 | 0.009122 | 7.134 | 708.7 | 0.1516 | 77.84 |
| Toledo | 112.3 | 0.002002 | 8.56 | 231.4 | 0.2231 | 27.5 |
| RC-K8 | 115.7 | 0.003371 | 10.06 | 349.2 | 0.07435 | 26.31 |
| SU-DHL-8 | 119.5 | 0.4857 | 2.081 | 363.2 | 0.6025 | 85.44 |
| OCI-LY10 | 125.3 | 0.01417 | 10.16 | 188.9 | 0.3202 | 22.31 |
| SU-DHL-16 | 149.7 | 0.1545 | 7.137 | 492.6 | 0.6619 | 60.79 |
| U-2932 | 163.7 | 0.03595 | 12.8 | 212.8 | 0.5669 | 25.81 |
| WILL-1 | 233.7 | 0.8166 | 4.216 | 549.4 | 2.515 | 79.51 |
| SU-DHL-4 | 296.2 | 0.2777 | 23.44 | 209 | 0.7823 | 25.33 |
| Pfeiffer | 313.5 | 0.04768 | 24.49 | 493.3 | 0.0136 | 51.82 |
| U-2904 | 334.1 | 0.2006 | 7.609 | 456.1 | 3.294 | 77.39 |
| WSU-DLCL | 341.9 | 0.142 | 27.83 | 565.1 | 0.01804 | 59.91 |
| HT | 396.7 | 0.3192 | 30.39 | 225.3 | 0.06622 | 25.16 |
| RIVA | 452.6 | 0.1135 | 36.65 | 242.8 | 0.01774 | 27.92 |
| ROS-50 | 762.1 | 10 | 65.57 | 87.92 | 0.3347 | 10.9 |
| U-2973 | 853.4 | 6.776 | 19.45 | 391.9 | 2.161 | 60.8 |
| DB | 941.4 | 10 | 89.46 | 80.31 | 0.06883 | 11.62 |
| OCI-LY7 | 48.18 | 0.006477 | 4.191 | 682.7 | 0.01627 | 71.18 |
| OCI-LY3 | 965.1 | 10 | 85.63 | 24.63 | 0.000263 | 4.493 |
| DOHH2 | 6.902 | 0.002801 | 0.2066 | 923.9 | 0.01753 | 95.1 |
| RL | 234.8 | 0.008755 | 21.55 | 115.9 | 0.1566 | 13.93 |
| Mino | 62.67 | 0.005782 | 5.638 | 968.2 | 0.002051 | 97.04 |
| Rec-1 | 281.8 | 0.03199 | 21.04 | 508.5 | 0.009258 | 57.27 |

AUC = area under the curve;
$IC_{50}$ = 50% inhibitory concentration (μM);
$E_{max}$ = maximum efficacy eliminating tumor cells achieved;
$Y_{max}$ = calculated percent of control at highest concentration of Compound 1.

Cell Proliferation and Viability Assay Using DLBCL Cell Lines with Acquired Resistance to Doxorubicin:

The following exemplary anti-proliferative assay uses exemplary DLBCL cell lines with acquired resistance to doxorubicin (Table 7). The in vitro growth inhibitory activity of Compound described herein was evaluated using a 384-well flow cytometry assay. The activity of Compound 1 was also evaluated in cell lines with acquired resistance to doxorubicin (one of the curative agents in the DLBCL standard of care regimen R-CHOP [rituximab, cyclophosphamide, doxorubicin, vincristine, and prednisone]) (Table 7).

TABLE 7

DLBCL Cell Lines with Acquired Resistance to Doxorubicin and Parental Cell Lines.

| Cell Line | Cell Culture Media |
|---|---|
| OCI-LY-10 Parental | RPMI + 10% FBS, 1X NEAA, |
| OCI-LY-10 DoxoR | 2 mM L-glutamine |
| WSU-DLCL2 Parental | |
| WSU-DLCL2 DoxoR | |
| SU-DHL-4 Parental | |
| SU-DHL-4 DoxoR | |
| U2932 Parental | RPMI + 10% FBS, 1X NEAA, |
| U2932 DoxoR | 2 mM L-glutamine |

FBS = fetal bovine serum;
NEAA = non-essential amino acid;
RPMI = RPMI1640;
DoxoR = cell lines with acquired resistance to doxorubicin.

The cell lines in Table 7 were plated in 96-well flat bottom plates and assessed with increasing concentrations of compound ranging from 0.0015 to 10 µM or dimethyl sulfoxide (DMSO) control. The final concentration of DMSO was 0.1% (v/v). Following the addition of Compound 1 or DMSO and incubation for 120 hours, cell number and cell death were analyzed by flow cytometry (Attune®, Thermo Fisher) using Annexin V and the vital dye, 7-AAD. Phosphatidylserine translocates from the inner layer to the outer layer of the cell membrane early in apoptosis and Annexin V binds to the exposed phosphatidylserine found on the surface of an apoptotic cell. The dye 7-AAD is excluded by intact live cells and only stains cells that have died as a result of apoptosis or necrosis.

Flow cytometry data analysis was then performed using the Flow Jo_v10 software to determine the number of viable cells (Annexin V and 7-AAD double negative staining cells) and percentage of apoptotic cells (Annexin V positive cells) for each condition. The live cell count for every concentration was normalized to the DMSO control (considered as 100%) to calculate the percentage of viable cells remaining after treatment and graphed using GraphPad Prism 7.03. The $IC_{50}$ (50% inhibitory concentration) and $E_{max}$ (maximum efficacy eliminating tumor cells achieved) values were then calculated by performing nonlinear regression curve fitting using log(inhibitor) vs. normalized response—variable slope analysis on GraphPad Prism 7.03. Area under the curve (AUC) was calculated by performing area under curve analysis on GraphPad Prism 7.03. Similarly, for apoptosis analysis, the percentage of apoptosis combining both "early" (Annexin V positive and 7-AAD negative) and "late" apoptosis (Annexin V and 7-AAD positive) cell gates relative to DMSO was graphed using GraphPad Prism 7.03. The AUC, $EC_{50}$ (concentration of Compound 1 that produces half-maximal apoptosis response) and $Y_{max}$ (maximal percentage of apoptosis achieved) values from apoptosis curves were calculated by performing area under curve analysis and nonlinear regression curve fitting using log(agonist) vs. normalized response—Variable slope analysis on GraphPad Prism 7.03.

In Table 8, dose-response proliferation curves for the cell lines with acquired resistance to doxorubicin and non-linear curve-fit regression were used to determine $IC_{50}$, AUC, and $E_{max}$ for % viable cells ($E_{max}$ for viability varies between 100 at low doses and 0 at high doses, which corresponds to inhibition of all viable cells), and dose-response apoptosis curves were used to determine the $EC_{50}$, AUC, and $Y_{max}$ for % apoptosis ($Y_{max}$ for apoptosis varies from 0 at low doses and 100 at higher doses which corresponds to death of all cells). Tumor cells were exposed to serial dilutions (0.00015 to 10 µM) of Compound 1 or dimethyl sulfoxide (DMSO) control for 5 days. Viability and apoptosis for all cell lines was determined by Annexin V/7-aminoactinomycin D (7-AAD) flow cytometry. Compound 1 was found to have antiproliferative activity and apoptotic effect in NHL cell lines with acquired resistance to doxorubicin (Table 8).

TABLE 8

Antiproliferative Activity and Apoptotic Effect of Compound 1 in Cell Lines with Acquired Resistance to Doxorubicin.

| Cell Lines | | % Viable Cells | | | Apoptosis | | |
|---|---|---|---|---|---|---|---|
| | | AUC | $IC_{50}$ (µM) | $E_{max}$ | AUC | $EC_{50}$ | $Y_{max}$ |
| Oci-Ly10 | Parental | 285.5 | 0.2 | 52 | 13 | 0.81 | 10.12 |
| | DoxoR | 211.8 | 0.09 | 25 | 27 | 0.64 | 19.48 |
| U2932 | Parental | 193 | 0.03 | 28.4 | 45.5 | 0.44 | 30 |
| | DoxoR | 256 | 0.25 | 27.7 | 15.7 | 1.12 | 16 |
| WSU-DLCL2 | Parental | 166.7 | 0.01 | 28 | 51 | 0.32 | 29.5 |
| | DoxoR | 195.9 | 0.07 | 8.4 | 74.4 | 0.4 | 57 |
| SUDHL4 | Parental | 335 | NA | 75 | 6 | 0.2 | 3.7 |
| | DoxoR | 182.4 | 0.072 | 7.5 | 84 | 0.4 | 63.5 |

AUC = area under the curve;
$IC_{50}$ = 50% inhibitory concentration (µM);
$E_{max}$ = maximum efficacy eliminating tumor cells achieved;
NA = not achieved;
$Y_{max}$ = calculated percent of control at highest concentration of Compound 1;
DoxoR = cell lines with acquired resistance to doxorubicin.

Example 5: Cell-Based Assays Using Compound 1 in Combination with Rituximab

Rituximab (humanized chimeric anti-CD20 monoclonal antibody) is known to act through different mechanisms including antibody-dependent cell-mediated cytotoxicity (ADCC) and antibody-dependent cellular phagocytosis (ADCP). Effect of combination of Compound 1 with rituximab in DLBCL and FL cell lines was evaluated in vitro in these 2 modalities.

NK Mediated Cell Killing (ADCC):

Commercial purified NK cells isolated from human peripheral blood mononuclear cell (PBMC) were seeded at a concentration of $10^6$ cells/mL, cultured in media supplemented with 10 ng/mLrhIL-2 and treated with Compound 1 (100 nM) for 18 hours at 37° C. prior to cytotoxicity assays. Target lymphoma cell lines were added to the pre-treated effector NK cells at a 1:10 (target:effector) cell ratio for WSU-DLCL2 and RL lines or 1:3 for SU-DHL6. At the time of co-culture, rituximab or isotype control at 7.5 ug/mL were added to the media and cells were incubated for 4 hours at 37° C. Then, cells were collected, stained with CD20, Annexin V and 7AAD and analyzed by FACS.

Macrophage Mediated Phagocytosis (ADCP):

Monocyte-derived macrophages (MDM) were generated by plating $8\times10^6$ commercial monocytes isolated from PBMC in RPMI media supplemented with 10% FBS, 1% L-glutamine and 60 ng/mL macrophage colony-stimulating factor (M-CSF) during 6 to 7 days. Then, MDM were treated with Compound 1 (10 nM) or DMSO control and cultured for an additional 48 hours prior to the assay. Lymphoma cell lines WSU-DLCL2, SU-DHL6 and RL were stained with CellTrace CFSE at 200 nM in PBS for 5 minutes at room temperature and added to the MDM cultures. At the time of co-culture, rituximab or isotype control were added to the media and cells were incubated at 37° C. during 3 hours. At the end of culture, cells were stained with anti-CD14 APC and images were acquired in Operetta. Phagocytosis index was calculated as cells positive for CFSE (green) and CD14 (red).

Results:

Effect of combination of Compound 1 with rituximab was analyzed in vitro exploring different aspects of rituximab mechanism of action.

ADCC bridges innate and adaptive immunity, and it involves both humoral and cellular immune responses. This mechanism has been adopted to create in-vitro cell-killing assays to ascertain the efficacy of therapeutic monoclonal antibodies such as rituximab to kill targeted tumor cells. This process triggers release of lytic proteins (perforins and proteases) from the effector cell that enter the tumor cell and kills it through lytic mediated apoptosis. As shown in FIG. 1, Compound 1 was able to increase rituximab cytotoxicity of lymphoma cell lines. This effect was more evident in cell lines with low response to rituximab single agent such as WSU-DLCL2. A maximum of about 40% toxicity induced was observed in this assay that may limit the results observed in SU-DHL6.

Figure 2:
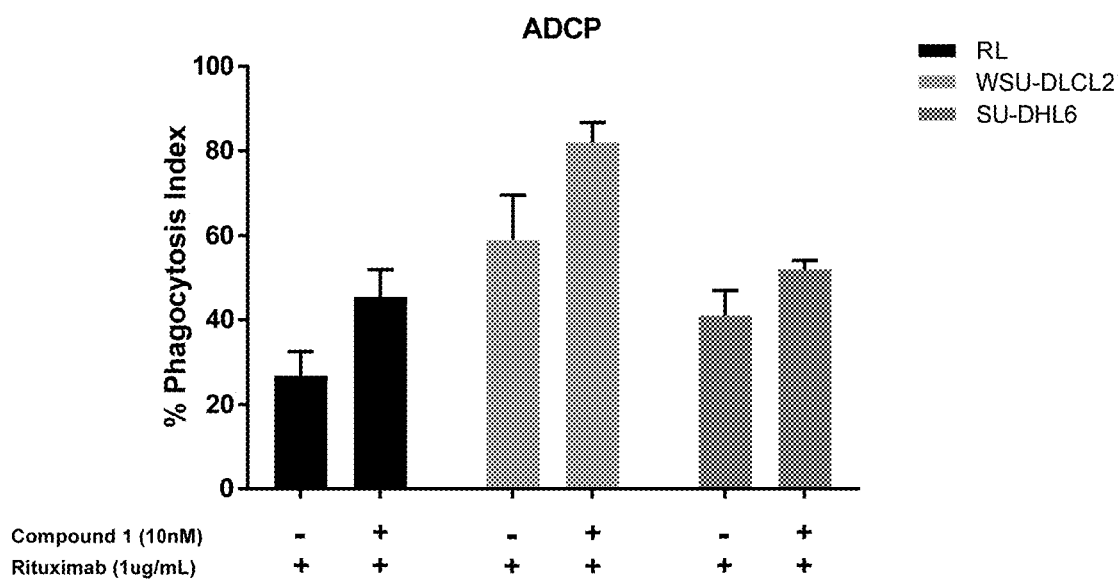
FIG. 2 illustrates macrophage mediated phagocytosis of the combination of Compound 1 and rituximab in lymphoma cell lines WSU-DLCL2, SU-DHL6, and RL.

ADCP is one crucial mechanism of antibody therapies such as rituximab. It is defined as a highly regulated process by which antibodies eliminate bound targets via connecting its Fc domain to specific receptors on phagocytic cells and eliciting phagocytosis. ADCP can be mediated by monocytes, macrophages, neutrophils, and dendritic cells but macrophages represent the predominant pathway. As shown in FIG. 2, at concentration of 1 g/mL of rituximab, addition of Compound 1 enhances phagocytosis of lymphoma cell lines mediated by macrophages.

The combination of rituximab with Compound 1 enhanced rituximab mediated toxicity not only by direct induction of apoptosis but also by increasing ADCC and ADCP. Moreover, the combination may benefit both DLBCL and FL.

Example 6: In Vivo Assays

The following are examples of in vivo assays that can be used to determine the effect of combination of compounds described herein with rituximab using exemplary non-Hodgkin's lymphoma (NHL) cells, for example DLBCL and FL cell lines.

General Procedures:

The following exemplary general procedures can be followed.

Cells:

WSU-DLCL2 (DLBCL), SUDHL-6 (DLBCL) and RL (FL) cells were obtained from ATCC and cultured in the medium recommended by ATCC.

Animals:

Female 6- to 8-weeks-old CB17 SCID mice were obtained from Charles River Laboratories. Mice were housed in a barrier facility in micro-isolator cages at 10 animals per cage. Mice were fed with Harlan-Teklad LM-485 Mouse/Rat Sterilizable Diet and autoclaved water ad libitum and maintained on a 12 hours light-dark cycle. Animals were acclimatized to the animal housing facility for a period of 7 days before the beginning of the experiment. All animal studies were performed under protocols approved by Institutional Animal Care and Use Committees.

Formulation:

Suspensions of Compound 1 were pared in aqueous 0.5% Methyl Cellulose, 0.25% Tween 80 and 50 mM Citrate pH 3. The formulations were homogenized using a Teflon pestle and mortar (Potter-Elvehjem tissue grinder). For multiday studies, the compound was freshly formulated every day. Compound 1 and vehicle were administered by oral gavage. Rituximab was diluted in 0.9% saline and administered intraperitoneally.

Xenograft Tumor Model:

Tumor cells were injected subcutaneously in the flank region above the right hind legs of female CB17 SCID mice. When the tumor volumes reach to approximately 200 $mm^3$, mice bearing tumors of 150-300 $mm^3$ were randomly assigned to receive oral doses of vehicle, Compound 1, rituximab or combination of Compound 1 (5 days on and 2 days off for 3 weeks) and rituximab (twice a week) for the duration of the study. Tumor volumes were determined before the initiation of treatment and were considered as the starting volumes. Tumors were measured twice a week for the duration of the study. The long and short axes of each tumor were measured using a digital caliper in millimeters. The tumor volumes were calculated using the formula: $width^2 \times length/2$. The tumor volumes were expressed in cubic millimeters ($mm^3$).

Statistical Analysis:

Xenograft data are expressed as mean±SEM. Statistical analyses were performed using GraphPad Prism. A one-way or two-way ANOVA was performed for tumor volume and PD marker measurements. Post hoc analysis was performed using the Dunnett test where all treatment groups are compared with the vehicle control. To determine the significance of combination treatments when compared with single agent alone, a two-way ANOVA was performed for tumor volume measurements with a post-hoc analysis using Bonferroni's test where all combination treatment groups are compared with the single agent treatment groups. Synergy calculations were made using the fractional product method. The following equation was used fu (1,2)=fu (1)×fu (2), where fu is the product of the unaffected fractions after treatment with either drug alone (Webb, J. L., Enzyme and Metabolic Inhibitors, Academic Press, New York, 1963).

Antitumor Activities in the WSU-DLCL2 (DLBCL) Xenograft Model:

Anti-tumor activity of Compound 1 alone and in combination with rituximab in WSU-DLCL2 (DLBCL) xenograft model were studied.

Xenograft study was conducted with female SCID mice bearing WSU-DLCL2 DLBCL xenograft tumors. Female SCID mice were inoculated subcutaneously with WSU-DLCL2 cells in the flank region above the right hind leg. Following inoculation of animals, the tumors were allowed to grow to approximately 200 mm$^3$ prior to randomization. On day 13 following tumor cell inoculation, the mice bearing WSU-DLCL2 tumors ranging between 150 and 250 mm$^3$ were pooled together and randomized into various treatment groups. Compound 1 was formulated in 0.5% Methyl Cellulose, 0.25% Tween 80 and 50 mM Citrate pH 3 in water. Rituximab was diluted in 0.9% saline. Compound 1 (1 or 3 mg/kg) was orally administered with a 5 days on and 2 days off schedule for 3 weeks starting from day 13 after tumor cell inoculation. Rituximab (10 mg/kg) was intraperitoneally administered twice a week (BIW). In combination group the animals received Compound 1 (1 or 3 mg/kg/day) and rituximab (10 mg/kg twice a week) simultaneously for the duration of the study starting from day 13 after tumor cell inoculation. Tumors were measured twice a week using calipers and tumor volumes were calculated using the formula of $W^2 \times L/2$. Statistical analysis was performed using a one-way or 2-way analysis of variance (ANOVA). Synergy calculations were performed using fractional product method.

Figure 3A:
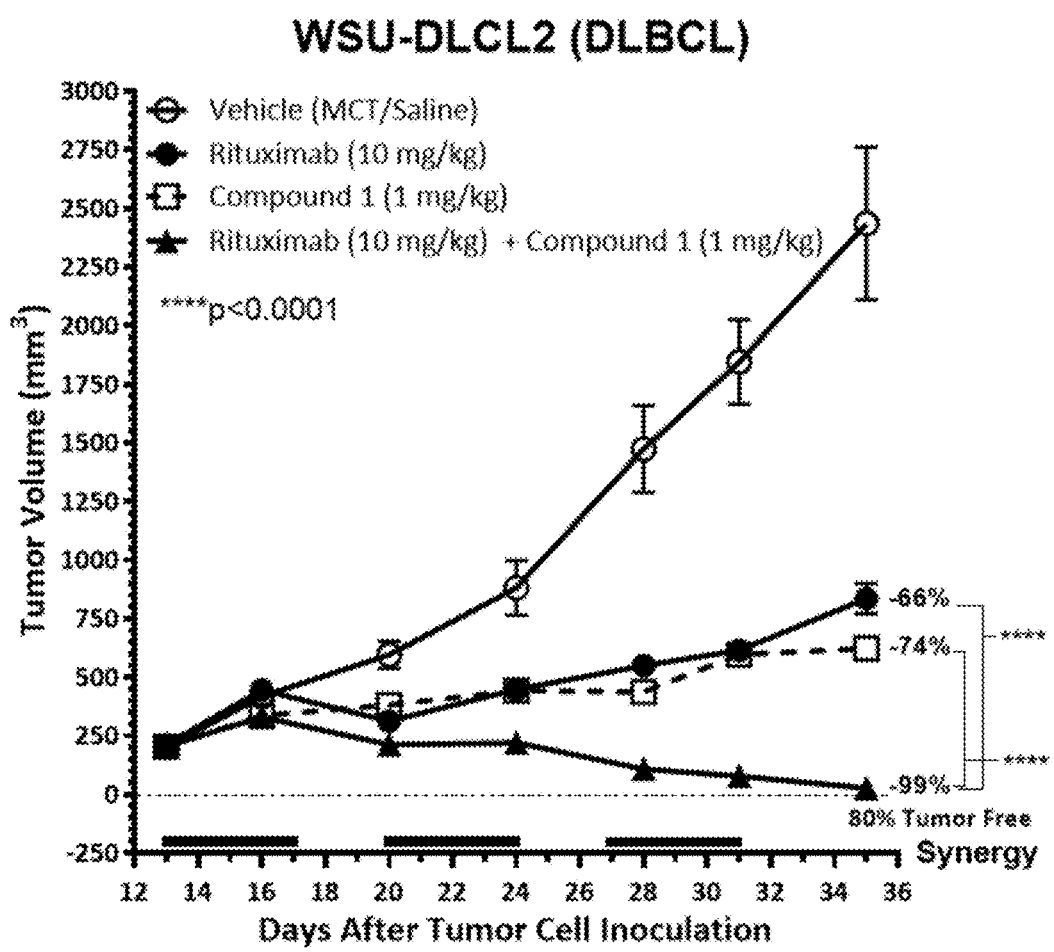
FIG. 3A and FIG. 3B illustrate anti-tumor activity of Compound 1 alone and in combination with rituximab in the WSU-DLCL2 (DLBCL) xenograft model, at the concentration of 1 mg/kg and 3 mg/kg of Compound 1, respectively.
Figure 3B:
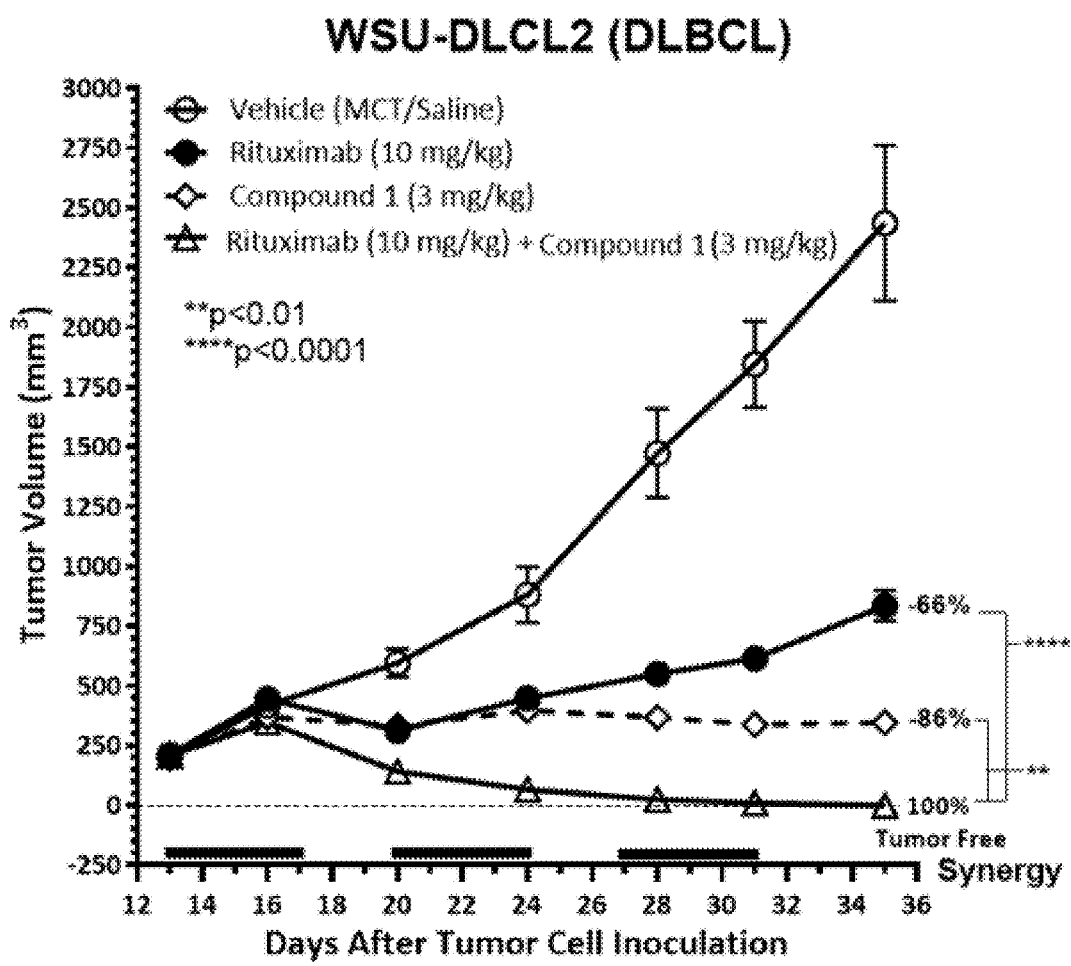

Compound 1 (1 or 3 mg/kg, qd) and rituximab (10 mg/kg, BIW) were tested as single agents and in combination in WSU-DLCL2 xenograft model, and the results are shown in FIG. 3A (Compound 1, 1 mg/kg) and FIG. 3B (Compound 1, 3 mg/kg). As a single agent Compound 1 at 1 and 3 mg/kg significantly (p<0.0001) inhibited WSU-DLCL2 DLBCL tumor growth with tumor volume reduction of 74 and 86%, respectively. Rituximab as single agent significantly (p<0.0001) inhibited (−66%) WSU-DLCL2 xenograft tumor growth. Compound 1 at 1 or 3 mg/kg when administered in combination with rituximab 10 mg/kg yielded a significant (p<0.0001) decrease in tumor volume when compared with vehicle control, displaying a tumor volume reduction of 99 and 100%, respectively. 80% and 100% of the animals treated with rituximab in combination with 1 or 3 mg/kg Compound 1, respectively were tumor free. In a 2-way ANOVA with Bonferroni's post-test, this combination antitumor activity was significantly better than Compound 1 at 1 or 3 mg/kg alone (99% or 100% versus 74% or 86% TVR; p<0.01 or 0.001) or rituximab alone (99% or 100% versus 66% TVR; p<0.0001). Using the fractional product method, the combination antitumor activity of Compound 1 at 1 or 3 mg/kg and rituximab at 10 mg/kg was determined to be synergistic in decreasing tumor volume.

Compound 1 (1 or 3 mg/kg, qd) and rituximab (10 mg/kg, BIW, twice a week) inhibited WSU-DLCL2 DLBCL tumor growth. Combination treatment of Compound 1 and rituximab showed synergistic antitumor activity.

Antitumor Activities in the SUDHL-6 (DLBCL) Xenograft Model:

Anti-tumor activity of Compound 1 alone and in combination with rituximab in SUDHL-6 (DLBCL) xenograft model were studied.

Xenograft study was conducted with female SCID mice bearing SUDHL-6 DLBCL xenograft tumors. Female SCID mice were inoculated subcutaneously with SUDHL-6 cells in the flank region above the right hind leg. Following inoculation of animals, the tumors were allowed to grow to approximately 200 mm$^3$ prior to randomization. On day 19 following tumor cell inoculation, the mice bearing SUDHL-6 tumors ranging between 150 and 250 mm$^3$ were pooled together and randomized into various treatment groups. Compound 1 was formulated in 0.5% Methyl Cellulose, 0.25% Tween 80 and 50 mM Citrate pH 3 in water. Rituximab was diluted in 0.9% saline. Compound 1 (10 mg/kg) was orally administered with a 5 days on and 2 days off schedule for 3 weeks starting from day 19 after tumor cell inoculation. Rituximab (10 mg/kg) was administered intraperitoneally twice a week (BIW). In combination group the animals received Compound 1 (10 mg/kg/day) and rituximab (10 mg/kg twice a week) simultaneously for the duration of the study starting from day 19 after tumor cell inoculation. Tumors were measured twice a week using calipers and tumor volumes were calculated using the formula of $W^2 \times L/2$. Statistical analysis was performed using a one-way or 2-way analysis of variance (ANOVA). Synergy calculations were performed using fractional product method.

Figure 4:
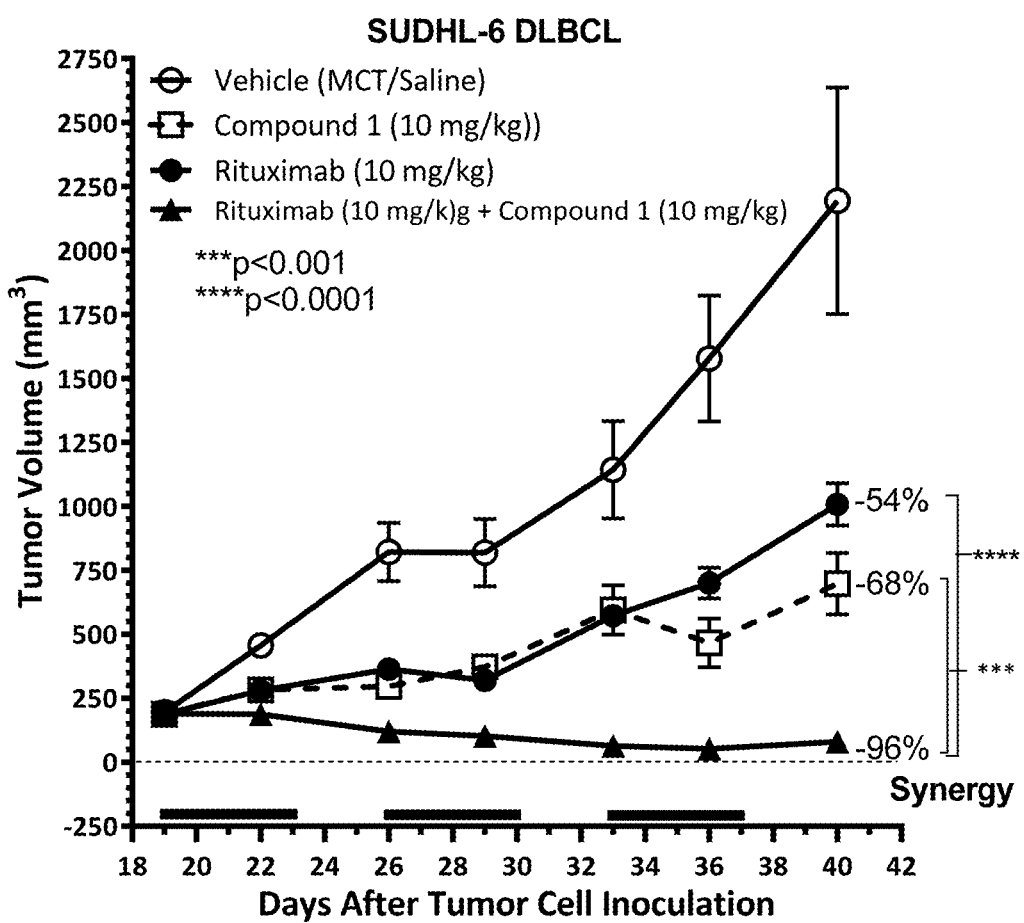
FIG. 4 illustrates anti-tumor activity of Compound 1 alone and in combination with rituximab in the SUDHL-6 (DLBCL) xenograft model.

Compound 1 (10 mg/kg, qd) and rituximab (10 mg/kg, BIW) were tested as single agents and in combination in SUDHL-6 xenograft model, and the results are shown in FIG. 4. As a single agent Compound 1 significantly (p<0.0001) inhibited (−68%) SUDHL-6 DLBCL tumor growth. Rituximab as single agent significantly (p<0.001) inhibited (−54%) SUDHL-6 xenograft tumor growth. Compound 1 at 10 mg/kg when administered in combination with rituximab 10 mg/kg yielded a significant (p<0.0001) decrease in tumor volume when compared with vehicle control, displaying a tumor volume reduction of 96%. In a 2-way ANOVA with Bonferroni's post-test, this combination antitumor activity was significantly better than Compound 1 alone (96% versus 68% TVR; p<0.001) or rituximab alone (96% versus 54% TVR; p<0.0001). Using the fractional product method, the combination antitumor activity of Compound 1 at 10 mg/kg and rituximab at 10 mg/kg was determined to be synergistic in decreasing tumor volume.

Compound 1 (10 mg/kg, qd) and rituximab (10 mg/kg, BIW, twice a week) inhibited SUDHL-6 DLBCL tumor growth. Combination treatment of Compound 1 and rituximab showed synergistic antitumor activity.

Antitumor Activities in the RL (Follicular Lymphoma) Xenograft Model:

Anti-tumor activity of Compound 1 alone and in combination with rituximab in RL (follicular lymphoma) xenograft model were studied.

Xenograft study was conducted with female SCID mice bearing RL follicular lymphoma xenograft tumors. Female SCID mice were inoculated subcutaneously with RL cells in the flank region above the right hind leg. Following inoculation of animals, the tumors were allowed to grow to approximately 200 mm$^3$ prior to randomization. On day 19 following tumor cell inoculation, the mice bearing RL tumors ranging between 150 and 250 mm$^3$ were pooled together and randomized into various treatment groups.

Compound 1 was formulated in 0.5% Methyl Cellulose, 0.25% Tween 80 and 50 mM Citrate pH 3 in water. Rituximab was diluted in 0.9% saline. Compound 1 (0.3 mg/kg) was orally administered with a 5 days on and 2 days off schedule for 3 weeks starting from day 19 after tumor cell inoculation. Rituximab (25 mg/kg) was administered intraperitoneally twice a week (BIW). In combination group the animals received Compound 1 (0.3 mg/kg/day) and rituximab (25 mg/kg twice a week) simultaneously for the duration of the study starting from day 19 after tumor cell inoculation. Tumors were measured twice a week using calipers and tumor volumes were calculated using the formula of $W^2 \times L/2$. Statistical analysis was performed using a one-way or 2-way analysis of variance (ANOVA). Synergy calculations were performed using fractional product method.

Figure 5:
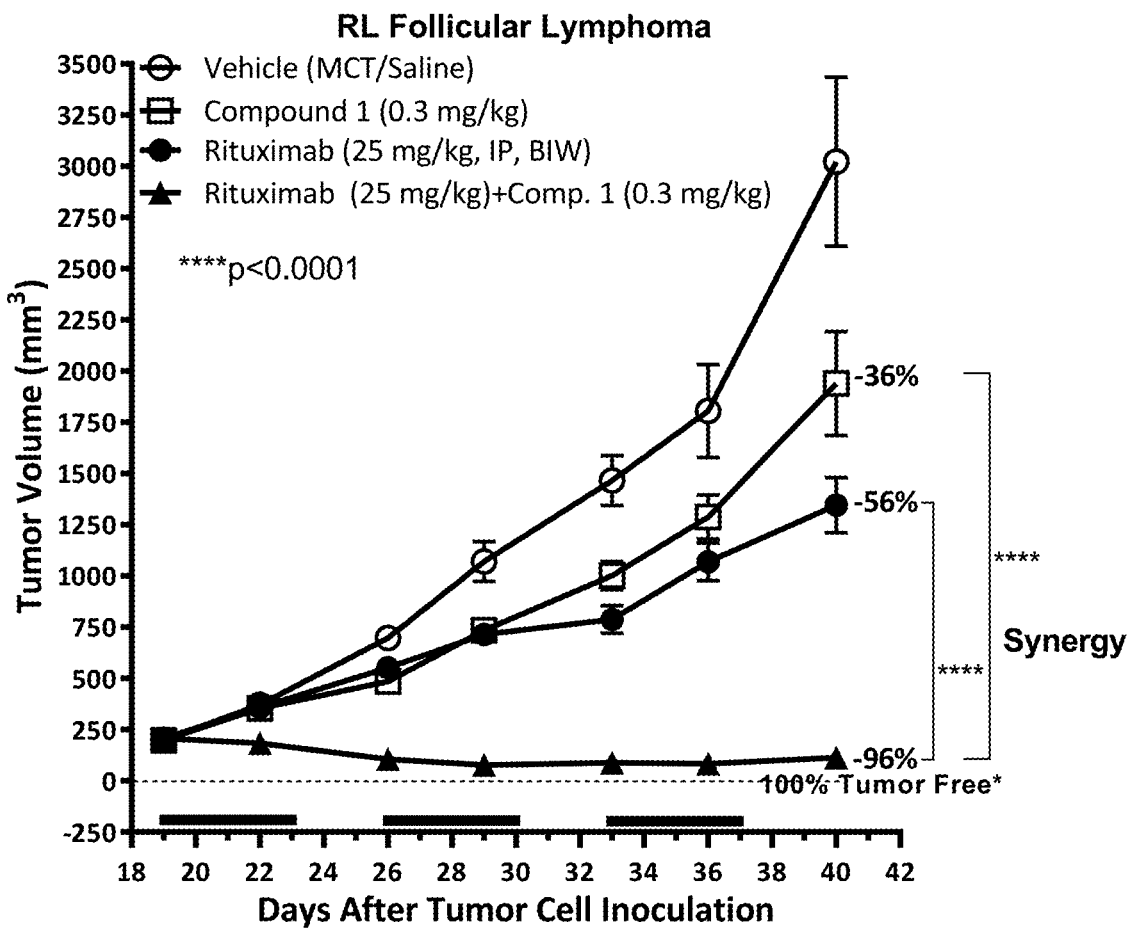
FIG. 5 illustrates anti-tumor activity of Compound 1 alone and in combination with rituximab in the RL (follicular lymphoma) xenograft model.

Compound 1 (0.3 mg/kg, qd) and rituximab (25 mg/kg, BIW) were tested as single agents and in combination in RL xenograft model, and the results are shown in FIG. 5. As a single agent Compound 1 significantly ($p<0.01$) inhibited (−36%) RL follicular lymphoma tumor growth. Rituximab as single agent significantly ($p<0.001$) inhibited (−56%) RL xenograft tumor growth. Compound 1 at 0.3 mg/kg when administered in combination with rituximab 25 mg/kg yielded a significant ($p<0.0001$) decrease in tumor volume when compared with vehicle control, displaying a tumor volume reduction of 96% compared to vehicle control. All of the animals in combination group were tumor free (tumor free defined as animals with <50 mm$^3$ tumor). In a 2-way ANOVA with Bonferroni's post-test, this combination antitumor activity was significantly better than Compound 1 alone (96% versus 36% TVR; $p<0.0001$) or rituximab alone (96% versus 56% TVR; $p<0.0001$). Using the fractional product method, the combination antitumor activity of Compound 1 at 0.3 mg/kg and rituximab at 25 mg/kg was determined to be synergistic in decreasing tumor volume.

Compound 1 (0.3 mg/kg, qd) and rituximab (25 mg/kg, BIW, twice a week) inhibited RL follicular lymphoma tumor growth. Combination treatment of Compound 1 and rituximab showed synergistic antitumor activity.

Example 7: In Vivo Model for CNS Lymphoma

Figure 6:
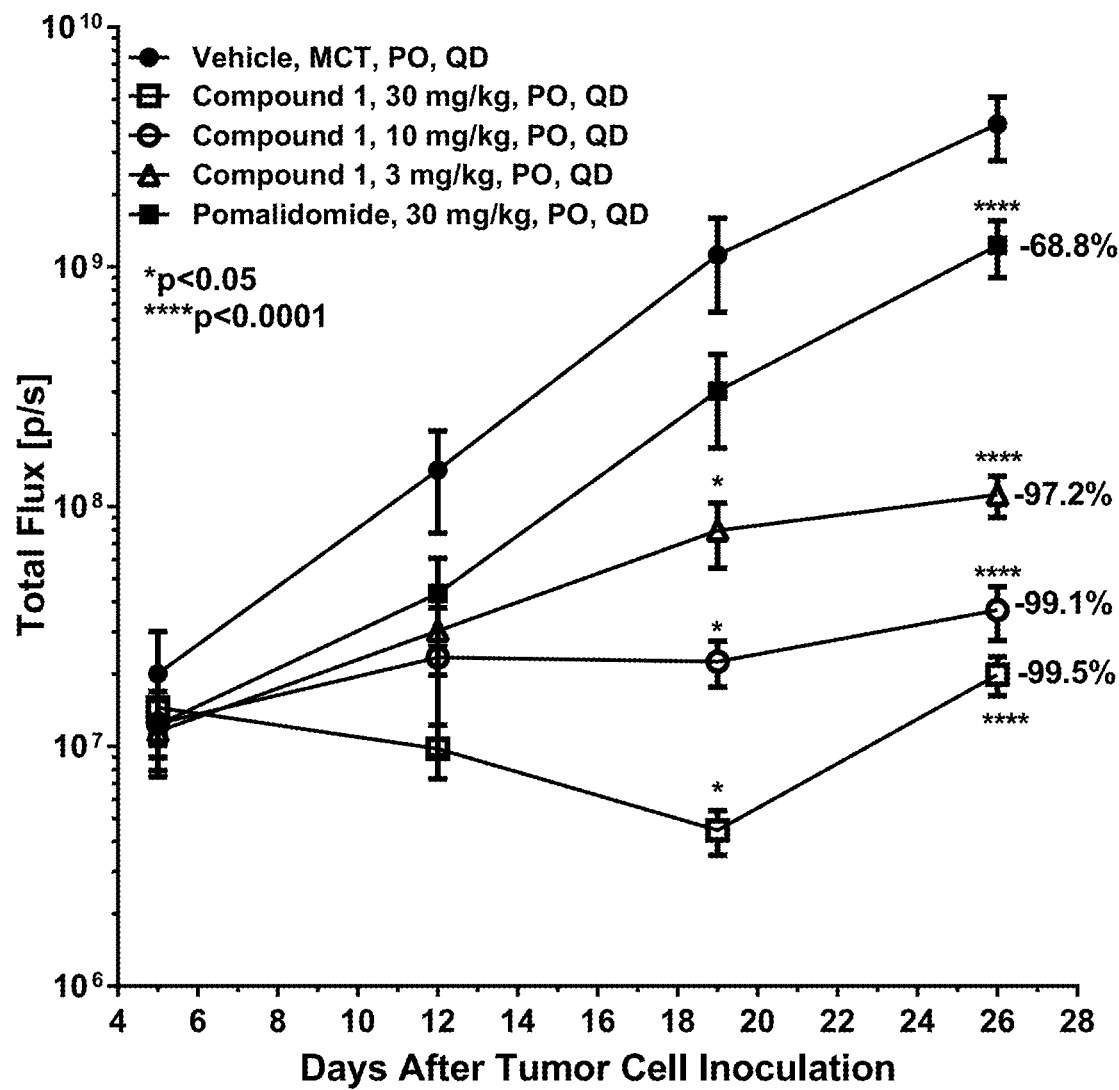
FIG. 6 illustrates anti-tumor activity of Compound 1 in OCI-LY-10-Luc CNS lymphoma xenograft model.
Figure 7:
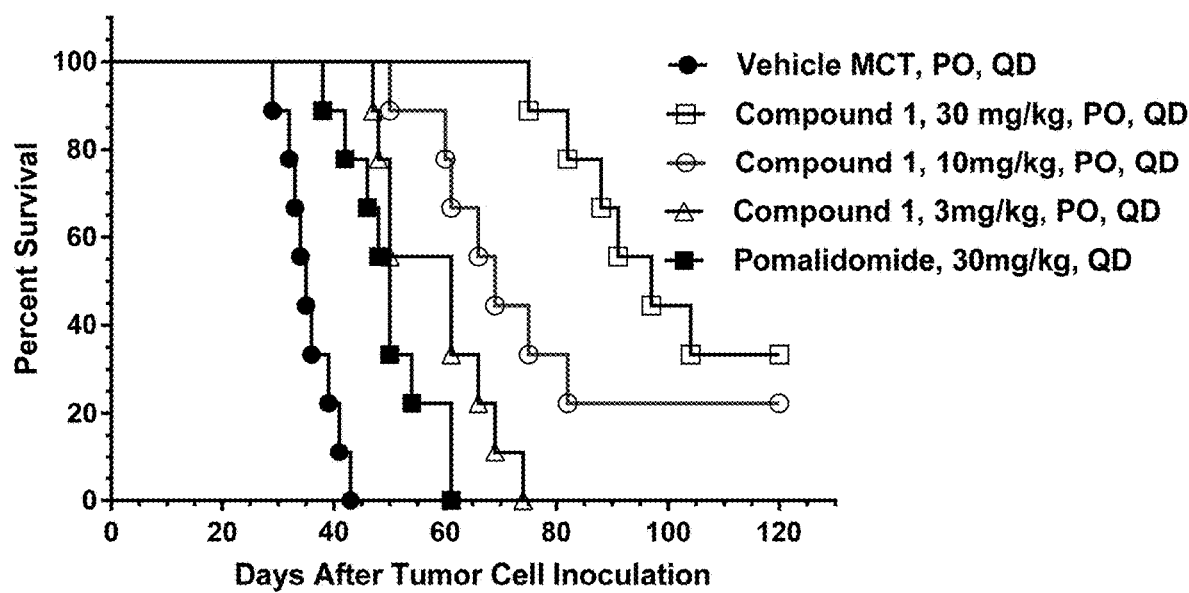
FIG. 7 illustrates anti-tumor activity (Survival curve) of Compound 1 in OCI-LY-10-Luc CNS lymphoma xenograft model.

Antitumor activity of Compound 1 was evaluated as a single agent in OCI-LY10-luc diffuse large B-cell lymphoma (DLBCL) xenografted intracranially into nude mice as a model for central nervous system (CNS) lymphoma.
Methods:

CNS lymphoma study was conducted with OCI-LY-10 cells transfected with luciferase (OCI-LY-10-Luc). Nude (nu/nu) mice were inoculated intracranially into the right cerebral hemisphere of the brain with OCI-LY10-Luc cells. Following inoculation of animals, the tumors were allowed to grow for 5 days. On day 5 following tumor cell inoculation, the mice were imaged using IVIS100 imaging system. The mice having tumors with an average flux ranging between $1 \times 10^7$ and $2 \times 10^7$ photons/sec were pooled together and randomized into various treatment groups. Compound 1 was formulated in 0.5% Methyl Cellulose, 0.25% Tween 80 and 50 mM Citrate pH 3 (MCT) in water. The animals were orally administered vehicle (MCT) or Compound 1 once daily (QD) for 3 weeks. Doses of Compound 1 ranged between 3 and 30 mg/kg. The positive control pomalidomide (30 mg/kg, QD) formulated in aqueous 0.5% CMC and 0.25% Tween-80 was administered PO. The animals were imaged for bioluminescence once a week using IVIS100 imaging system and monitored for survival. Statistical analysis was performed using a log-rank test between Compound 1-treated and vehicle-treated control groups.
Results & Conclusions:

To evaluate the response of established B-cell lymphoma in the brain to therapeutic intervention with Compound 1 in vivo, the real time tumor growth in the brain was assessed by bioluminescence imaging (FIG. 6), followed by survival analysis (FIG. 7). Compound 1 at 3, 10 or 30 mg/kg, qd was tested as single agent with once a day (QD) dosing for 3 weeks starting from day 5 after OCI-LY-10-Luc tumor cell inoculation into the brain. Pomalidomide was used as positive control. Treatment of animals with Compound 1 resulted in substantial reduction of tumor burden as evidenced by reduction and diminished bioluminescence signal in a dose-dependent fashion (FIG. 6; Table 9). In a Kaplan-Meier survival analysis, the median survival of the vehicle treated animals was 35 days. The animals in Compound 1 at 30, 10 and 3 mg/kg treated groups survived significantly ($p<0.0001$; long-rank test) longer than vehicle control group with a median survival of 97, 69 and 61 days, respectively (FIG. 7; Table 9). By the time of the termination of the experiment on day 120, there were 33.3% (3/9) and 22.2% (2/9) animals survived with no detectable bioluminescence signal at 30 and 10 mg/kg doses, respectively. In conclusion, Compound 1 as a single agent exhibited a dose-response relationship for reducing the tumor burden and prolonged the survival of mice in the OCI-LY10 CNS lymphoma xenograft model.

TABLE 9

Percentage of Bioluminescence inhibition on Day 26 and survival analysis Following Treatment with Compound 1 in OCI-LY10-Luc CNS DLBCL Xenograft Model

| Treatment | Dose (mg/kg) | Schedule | % BLI Inhibition on Day 26 | P value on Day 26 (BLI) | Median Survival (Days) | P value (Survival) (log-rank test) |
|---|---|---|---|---|---|---|
| Vehicle | — | QD | 0 | — | 35 | — |
| Compound 1 | 30 | QD | 99.5% | <0.0001 | 97 | <0.0001 |
| Compound 1 | 10 | QD | 99.1% | <0.0001 | 69 | <0.0001 |
| Compound 1 | 3 | QD | 97.2% | <0.0001 | 61 | <0.0001 |
| Pomalidomide | 30 | QD | 68.8% | <0.0001 | 50 | <0.001 |

BLI = bioluminescence;
QD = once a day;
Percent bioluminescence was calculated relative to the vehicle control on day 26.

Example 8: In Vivo Model for Follicular Lymphoma

Anti-tumor activity of Compound 1 was evaluated as monotherapy (between 1 and 30 mg/kg, qd) in RL (follicular lymphoma) xenograft model.

Methods:

Xenograft study was conducted with female SCID mice bearing RL follicular lymphoma xenograft tumors. Female SCID mice were inoculated subcutaneously with RL cells in the flank region above the right hind leg. Following inoculation of animals, the tumors were allowed to grow to approximately 200 mm$^3$ prior to randomization. On day 14 following tumor cell inoculation, the mice bearing RL tumors ranging between 150 and 250 mm$^3$ were pooled together and randomized into various treatment groups. Compound 1 was formulated in 0.5% Methyl Cellulose, 0.25% Tween 80 and 50 mM Citrate pH 3 in water. Compound 1 at 1, 3, 10 or 30 mg/kg was orally administered once daily with a 5 days on and 2 days off schedule for 3 weeks starting from day 14 after tumor cell inoculation. Tumors were measured twice a week using calipers and tumor volumes were calculated using the formula of $W^2 \times L/2$. Statistical analysis was performed using a one-way or 2-way analysis of variance (ANOVA). Synergy calculations were performed using fractional product method.

Figure 8:
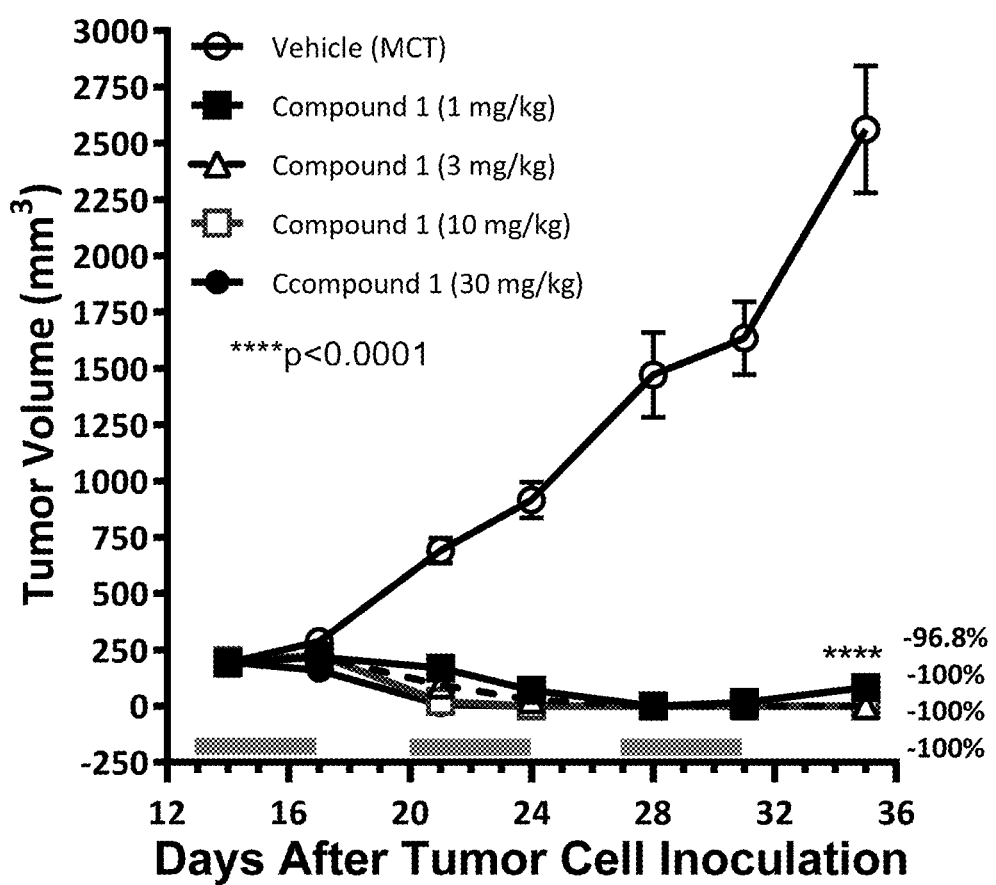
FIG. 8 illustrates single agent antitumor activity of Compound 1 in RL follicular lymphoma.

Results & Conclusions: The results are shown in FIG. 8. As a single agent Compound 1 at 1 mg/kg (lowest dose tested) significantly (p<0.0001) inhibited (−96.8%) RL follicular lymphoma tumor growth. At higher doses of 3, 10 and 30 mg/kg of Compound 1, the tumor growth was completely inhibited and all the animals became tumor free. In conclusion, Compound 1 as a monotherapy completely inhibited follicular lymphoma tumor growth and produced tumor free animals in RL follicular lymphoma xenograft model.

Example 9: Phase I Clinical Study

A phase 1, multi-center, open-label study is conducted to assess the safety, pharmacokinetics and preliminary efficacy of Compound 1 alone and in combination with rituximab in subjects with relapsed or refractory (R/R) NHL, such as relapsed or refractory diffuse large B-cell lymphoma (R/R DLBCL), relapsed or refractory follicular lymphoma (R/R FL), relapsed or refractory primary central nervous system lymphoma (R/R PCNSL), and relapsed or refractory mantle cell lymphoma (R/R MCL).

Objectives:

A primary objective of the study is to determine the safety and tolerability of Compound 1 alone and in combination with rituximab in subjects with R/R NHL. Another primary objective is to define the maximum tolerated dose (MTD) and/or the recommended Phase 2 dose (RP2D) of Compound 1 in subjects with R/R NHL.

The secondary Objectives are to characterize the pharmacokinetics (PK) of Compound 1 and to provide information on the preliminary efficacy of Compound 1 alone and in combination with rituximab in R/R NHL.

Study Design:

This is an open-label, Phase 1, dose escalation (Part A) and dose expansion (Part B), first-in-human (FIH) clinical study of Compound 1 administered orally alone and in combination with rituximab. Compound 1 is given as monotherapy in subjects with R/R NHL, which includes DLBCL (not otherwise specified [NOS] or transformed), FL, MCL or PCNSL who have failed at least 2 lines of therapy (or who have received at least one prior line of standard therapy and are not eligible for any other therapy). Compound 1 is tested as a combination with rituximab in R/R DLBCL and R/R FL subjects. The dose escalation (Part A) evaluates the safety and tolerability of escalating doses of Compound 1 in R/R DLBCL and R/R FL to determine the MTD of Compound 1 as a monotherapy. An accelerated titration design is utilized at the initial dose levels; afterward, a two-parameter Bayesian logistic regression model (BLRM) utilizing escalation with overdose control (EWOC) (Babb J, Rogatko A, Zacks S. Cancer phase I clinical trials: efficient dose escalation with overdose control. *Stat Med* 1998; 17(10):1103-20; Neuenschwander B, Branson M, Gsponer T. Critical aspects of the Bayesian approach to phase I cancer trials. *Stat Med* 2008; 27(13); 2420-39), helps guide Compound 1 dose escalation/de-escalation decisions.

Part B further evaluates the safety and efficacy of Compound 1 administered at or below the MTD alone or in combination with rituximab, administered intravenously (IV), in selected expansion cohorts of up to approximately 20 evaluable subjects each in R/R DLBCL, FL, MCL or PCNSL, in order to determine the RP2D. The combination of Compound 1 and rituximab is tested in subjects with R/R DLBCL or R/R FL.

Compound 1 is administered orally once daily (QD) on planned dosing days. Part B expansion cohorts tests different doses and/or schedules of Compound 1 based on the safety and tolerability determined in Part A. All treatments are administered in 28-day cycles until clinically-significant disease progression, unacceptable toxicity, or subject/physician decision to withdraw.

Following completion of dose escalation (Part A), selected expansion cohorts of approximately 20 efficacy evaluable subjects per cohort receive Compound 1 alone or in combination with rituximab. Expansion may occur at the MTD established in the Part A and/or at a lower dose, or an alternative tolerable dosing schedule, based on review of available safety, PK, and PD data.

The study is conducted in compliance with International Conference on Harmonisation (ICH) Good Clinical Practices (GCPs).

Study Population:

Subjects (male or female), ≥18 years of age, with R/R NHL who have relapsed after, progressed on (or not been able to tolerate due to medical comorbidities or unacceptable toxicity) standard anticancer therapy, or for whom no other approved conventional therapy exists, are enrolled in the study.

Inclusion Criteria:

Subjects must satisfy the following criteria to be enrolled in the study:

1. Subject is ≥18 years of age at the time of signing the informed consent form (ICF).

2. Subject must understand and voluntarily sign an ICF prior to any study-related assessments/procedures being conducted.

3. Subject is willing and able to adhere to the study visit schedule and other protocol requirements.

4. Subject has a history of NHL (including DLBCL, FL, MCL, and PCNSL) with relapsed or refractory disease according to one of the following definitions:

a. For R/R DLBCL (not otherwise specified, [NOS]): following at least 2 prior lines of therapy OR have failed at least one prior line of standard therapy and are not eligible for SCT. Subjects with only one prior line of standard therapy must be ineligible for autologous SCT at the time of enrollment.

b. For R/R DLBCL (transformed lymphoma): following chemotherapy for lower grade lymphoma and at least one standard treatment regimen for DLBCL.
c. For R/R FL: following at least 2 prior lines of therapy and meet treatment criteria at the time of enrollment based on investigator's assessment (e.g., according to Groupe d'Etude des Lymphomes Folliculaires [GELF] criteria [National Comprehensive Cancer Network. NCCN Clinical Practice Guidelines in Oncology: B-cell Lymphomas; V.2.2018. 2018 Feb. 26; V.2. Available from: https://www.nccn.org/professionals/physician_gls/pdf/b-cell.pdf]).
d. For R/R MCL in Part B: following at least 2 prior lines of therapy.
e. For R/R PCNSL in Part B: following at least 2 prior lines of therapy.
5. Subjects must have measurable disease:
a. Bi-dimensionally measurable disease on cross sectional imaging by computed tomography (CT) or magnetic resonance imaging (MRI) with at least one lesion >1.5 cm in the transverse diameter, as defined by the Lugano classification of NHL (Cheson B D, Fisher R I, Barrington S F, Cavalli F, Schwartz L H, Zucca E, et al. Recommendations for initial evaluation, staging, and response assessment of Hodgkin and non-Hodgkin lymphoma: the Lugano classification. *J Clin Oncol.* 2014; 32(27):3059-3068).
Measurable disease cannot be previously irradiated.
b. PCNSL subjects in Part B must have disease that is objectively measurable by International Workshop to Standardize Baseline Evaluation and Response Criteria in Primary CNS Lymphoma (Abrey L E, Batchelow T T, et al. Baseline Evaluation and Response Criteria for Primary CNS Lymphoma. *JCO:* 2005, (23): 5034-5043), cerebrospinal fluid (CSF) cytology (in case of leptomeningeal only disease), or vitreal aspiration cytology and/or retinal photographs (in case of ocular lymphoma if clinically indicated).
6. Subject consents to retrieve formalin-fixed paraffin-embedded (FFPE) archival tumor tissue, either in tumor blocks or sectioned/mounted specimens, if collected within the last year and if using in place of the Screening biopsy for PD in Part A.
7. For subjects participating in Part A, subject consents to and has tumor accessible for tumor biopsy or FNA at Screening and FNA in Cycle 1; for Part B, subject consents to and has tumor accessible for paired tumor biopsies during Screening and Cycle 1.
8. Subject has an Eastern Cooperative Oncology Group (ECOG) performance status of 0, 1 or 2.
9. Subjects must have the following laboratory values:
a. Absolute neutrophil count (ANC)≥1.5×10$^9$/L without growth factor support for 7 days (14 days if pegfilgrastim).
b. Hemoglobin (Hgb)≥8 g/dL.
c. Platelets (plt)≥75×10$^9$/L without transfusion for 7 days.
d. Aspartate aminotransferase/serum glutamic oxaloacetic transaminase (AST/SGOT) and alanine aminotransferase/serum glutamate pyruvic transaminase (ALT/SGPT)≤2.5× upper limit of normal (ULN).
e. Serum bilirubin≤1.5×ULN except in cases of Gilberts Syndrome, then ≤2.0×ULN
f. Estimated serum creatinine clearance of ≥60 mL/min using the Cockcroft-Gault equation or directly determined from the 24-hour urine collection method.
g. International normalized ratio (INR)<1.5×ULN and partial thromboplastin time (aPTT)<1.5×ULN.
10. Subjects must agree not to donate blood while receiving Compound 1, during dose interruptions and for at least 28 days following the last dose of Compound 1.
11. Females of childbearing potential (FCBP) must:
a. Either commit to true abstinence from heterosexual contact (which must be reviewed on a monthly basis and source documented) or agree to use, and be able to comply with, at least 2 effective contraceptive methods (oral, injectable, or implantable hormonal contraceptive; tubal ligation; intra-uterine device; barrier contraceptive with spermicide; or vasectomized partner), one of which must be barrier, from signing the ICF, at least 28 days before starting Compound 1, throughout the study, and for up to 28 days following the last dose of Compound 1 and up to one year following the last dose of rituximab; and
b. Have 2 negative pregnancy tests as verified by the Investigator prior to starting Compound 1:
  a negative serum pregnancy test (sensitivity of at least 25 mIU/mL) at Screening (between 10 to 14 days prior to Cycle 1 Day 1).
  a negative serum or urine pregnancy test (Investigator's discretion) within 24 hours prior to Cycle 1 Day 1 of study treatment (note that the Screening serum pregnancy test can be used as the test prior to Day 1 study treatment if it is performed within the prior 24 hours).
c. Avoid conceiving for 28 days after the last dose of Compound 1.
d. Agree to ongoing pregnancy testing during the course of the study, and after the end of study treatment. This applies even if the subject practices true abstinence from heterosexual contact. (True abstinence is acceptable when this is in line with the preferred and usual lifestyle of the subject. In contrast, periodic abstinence (e.g., calendar, ovulation, symptothermal, post-ovulation methods) and withdrawal are not acceptable methods of contraception.)
e. Agree to refrain from donating ova while on Compound 1 for 30 days after its discontinuation.
f. Agree to abstain from breastfeeding or providing breast milk while on Compound 1 and for 28 days after its discontinuation.
12. Males must practice true abstinence (which must be reviewed on a monthly basis) or agree to use a condom (a latex condom is recommended) during sexual contact with a pregnant female or a FCBP and avoid conceiving from the date of signing the ICF, while participating in the study, during dose interruptions, and for at least 90 days following Compound 1 discontinuation, even if he has undergone a successful vasectomy.
a. Males must agree to refrain from donating semen or sperm while on Compound 1 and for 90 days after its discontinuation.

Exclusion Criteria:
The presence of any of the following excludes a subject from enrollment:
1. Subject has any significant medical condition, laboratory abnormality, or psychiatric illness that would prevent the subject from participating in the study.
2. Subject has any condition including the presence of laboratory abnormalities, which places the subject at unacceptable risk if he/she were to participate in the study.
3. Subject has any condition that confounds the ability to interpret data from the study.
4. Subject has life expectancy ≤2 months.
5. Subjects who have aggressive lymphoma relapse requiring immediate cytoreductive therapy to avoid potential life-threatening consequences (e.g., due to tumor location).
6. Subject has received prior systemic anti-cancer treatment (approved or investigational)≤5 half-lives or 4 weeks prior to starting Compound 1, whichever is shorter.

7. Subject has received prior CAR-T or other T-cell targeting treatment (approved or investigational)≤4 weeks prior to starting Compound 1.
8. Subject has received prior therapy with CRBN-modulating drug (e.g., lenalidomide, avadomide/CC-122, pomalidomide)≤4 weeks prior to starting Compound 1.
9. Subject is a pregnant or nursing female or intends to become pregnant during participation in the study.
10. Subject has symptomatic CNS involvement of disease (does not apply to PCNSL subjects in Part B).
11. Persistent diarrhea or malabsorption≥Grade 2 National Cancer Institute (NCI) Common Terminology Criteria for Adverse Events (CTCAE), despite medical management
12. Peripheral neuropathy≥NCI CTCAE Grade 2.
13. Subject is on chronic systemic immunosuppressive therapy or corticosteroids (e.g., prednisone or equivalent not to exceed 10 mg per day within the last 14 days) or subjects with clinically significant graft-versus-host disease (GVHD).
a. Stable use of inhaled corticosteroids is allowed.
b. The use of topical steroids for ongoing skin or ocular GVHD is permitted.
c. In Part B, PCNSL subjects taking glucocorticoids are allowed but must be on a stable dose for 7 days prior to Cycle 1 Day 1.
14. Subject has impaired cardiac function or clinically significant cardiac diseases, including any of the following:
a. Left ventricular ejection fraction (LVEF)<45% as determined by multigated acquisition scan (MUGA) or echocardiogram (ECHO).
b. Complete left bundle branch or bifascicular block.
c. Congenital long QT syndrome.
d. Persistent or clinically meaningful ventricular arrhythmias.
e. QTcF≥470 msec on Screening electrocardiogram (ECG; mean of triplicate recordings).
f. Unstable angina pectoris or myocardial infarction ≤3 months prior to starting.
15. Subject had prior autologous SCT≤3 months prior to starting Compound 1 and any treatment-related toxicity is unresolved (grade >1).
16. Subject had prior allogeneic SCT with either standard or reduced intensity conditioning ≤6 months prior to starting Compound 1 and any treatment-related toxicity is unresolved (grade >1).
17. Subject had major surgery ≤2 weeks prior to starting Compound 1. Subjects must have recovered from any clinically significant effects of recent surgery.
18. Prior radiotherapy within one month prior to starting study drug.
19. Subject has known human immunodeficiency virus (HIV) infection.
20. Subject has known chronic active hepatitis B or C virus (HBV/HCV) infection.
21. Subject has a history of concurrent second cancers requiring active, ongoing systemic treatment.
22. Concurrent administration of strong CYP3A4/5 modulators.

Length of Study:

The total study duration is expected to be approximately 4 to 5 years. Approximately 18 months is required to enroll and evaluate subjects in the dose escalation portion of the study (Part A). Approximately 12 to 18 months is required to enroll subjects in the Part B portion of the study. Completion of active treatment and post-treatment follow-up is expected to take an additional 12 to 24 months. The End of Trial is defined as either the date of the last visit of the last subject to complete the post-treatment follow-up, or the date of receipt of the last data point from the last subject that is required for primary, secondary and/or exploratory analysis, as pre-specified in the protocol, whichever is the later date.

Study Treatment:

Subjects are assigned to a dose level and cohort by the Sponsor based on the subject's eligibility and slot availability. Subjects assigned to Dose Levels in Part A and single agent cohorts receive Compound 1 as a monotherapy. Subjects assigned to Part B combination cohorts receive Compound 1 in combination with rituximab. Compound 1 is supplied as capsules for oral administration in appropriate dose strengths.

For subjects receiving rituximab in combination with Compound 1 in Part B, rituximab is administered (per package insert and institutional standard practice) on planned dosing days at the fixed dose of 375 mg/m$^2$. In Cycle 1, rituximab is given on Days 1, 8, 15, and 22; in Cycles 2-6, rituximab is given on Day 1 of each cycle, thereafter, rituximab is given once every 8 weeks thereafter (e.g., C8D1, C10D1, etc) until disease progression.

Overview of Key Efficacy Assessments:

The primary efficacy variable is tumor response rate. Tumor response are determined by the Investigator. For NHL, the International Workshop Criteria for Malignant Lymphoma (Cheson B D, et al. Recommendations for initial evaluation, staging, and response assessment of Hodgkin and non-Hodgkin lymphoma: the Lugano classification. *J Clin Oncol*. 2014; 32(27):3059-3068) and the Deauville Criteria for fluorodeoxyglucose-positron emission tomography (FDG-PET) scan interpretation (Itti E, et al. An international confirmatory study of the prognostic value of early PET/CT in diffuse large B-cell lymphoma: comparison between Deauville criteria and DeltaSUVmax. *Eur J Nucl Med Mol Imaging*. 2013 September; 40(9):1312-20; Meignan M, et al. Report on the 4th International Workshop on Positron Emission Tomography in Lymphoma held in Menton, *France*, 3-5 Oct. 2012. *Leuk Lymphoma*. 2014 January; 55(1):31-37) are used for efficacy assessment ("Lugano criteria"). Other response criteria are used as appropriate, including the International Workshop to Standardize Baseline Evaluation and Response Criteria in Primary CNS Lymphoma (Abrey L E, et al. Baseline Evaluation and Response Criteria for Primary CNS Lymphoma. *JCO:* 2005, (23): 5034-5043) for PCNSL. Efficacy variables to be analyzed include tumor response at the end of treatment, the proportion of subjects alive and progression-free, and duration of response.

Efficacy assessments include: clinical findings (e.g., physical examination, constitutional symptoms), contrast enhanced computed tomography (CT) scans where appropriate, FDG-PET/CT scans where appropriate, bone marrow examination (biopsy and aspiration) where appropriate, and Magnetic resonance imaging (MRI) where appropriate.

All treated subjects are included in the efficacy analyses.

A descriptive analysis of evidence of antitumor activity is provided based on clinical, laboratory, and radiographic assessments by the Investigator, which includes assessment of target lesions, non-target lesions, new lesions and overall response.

The efficacy variable of focus for Part A is objective response rate (ORR). Additional efficacy variables to be analyzed include time to response, duration of response, progression-free survival (PFS) and overall survival (OS).

Efficacy variables mature when the last subject in each cohort has withdrawn from the study or completed one year of treatment.

Secondary and exploratory endpoints include evaluation of Compound 1 PD and predictive biomarkers in blood and/or tumor, and exploration of PK, PD, toxicity, and activity relationships.

Overview of Key Safety Assessments:

Safety assessments include: monitoring for adverse events (AEs), physical examination, vital signs/weight, Eastern Cooperative Oncology Group (ECOG) performance status, safety laboratory assessments (including hematology and clinical chemistry, coagulation studies, and urinalysis), cardiac monitoring including 12-lead electrocardiograms (ECGs) and left ventricular ejection fraction (LVEF) assessments, concomitant medications, procedures, therapies, and pregnancy testing (for females of child bearing potential [FCBP]).

Overview of Pharmacokinetic Assessments:

The PK profiles of Compound 1 are determined from serial blood collections.

Example 10: Phase I Clinical Study

A phase 1, multi-center, open-label study is conducted to assess the safety, pharmacokinetics, and preliminary efficacy of Compound 1 alone and in combination with rituximab in subjects with relapsed or refractory non-Hodgkin lymphomas (R/R NHL), such as relapsed or refractory diffuse large B-cell lymphoma (R/R DLBCL), relapsed or refractory follicular lymphoma (R/R FL), relapsed or refractory primary central nervous system lymphoma (R/R PCNSL), and relapsed or refractory mantle cell lymphoma (R/R MCL).

Objectives: A primary objective of the study is to determine the safety and tolerability of Compound 1 alone and in combination with rituximab in subjects with R/R NHL. Another primary objective is to define the maximum tolerated dose (MTD) and/or the recommended Phase 2 dose (RP2D) of Compound 1 in subjects with R/R NHL.

The secondary objectives are to characterize the pharmacokinetics (PK) of Compound 1 and to provide information on the preliminary efficacy of Compound 1 alone and in combination with rituximab in R/R NHL.

Study Design:

This is an open-label, Phase 1, dose escalation (Part A) and dose expansion (Part B), first-in-human (FIH) clinical study of Compound 1 administered orally alone and in combination with rituximab. Compound 1 is given as a monotherapy in subjects with R/R NHL, which includes DLBCL (de novo or transformed), FL, MCL or PCNSL who have failed at least 2 lines of therapy (or who have received at least one prior line of standard therapy and are not eligible for any other therapy). Compound 1 is tested as a combination with rituximab in R/R DLBCL and R/R FL subjects. The dose escalation (Part A) evaluates the safety and tolerability of escalating doses of Compound 1 in R/R DLBCL and R/R FL to determine the MTD of Compound 1 as a monotherapy. An accelerated titration design is utilized at the initial dose levels; afterward, a two-parameter Bayesian logistic regression model (BLRM) utilizing escalation with overdose control (EWOC) (Babb J, Rogatko A, Zacks S. Cancer phase I clinical trials: efficient dose escalation with overdose control. *Stat Med* 1998; 17(10):1103-20; Neuenschwander B, Branson M, Gsponer T. Critical aspects of the Bayesian approach to phase I cancer trials. *Stat Med* 2008; 27(13); 2420-39), helps guide Compound 1 dose escalation/de-escalation decisions.

Part B further evaluates the safety and efficacy of Compound 1 administered at or below the MTD alone or in combination with rituximab, administered intravenously (IV), in selected expansion cohorts of up to approximately 20 evaluable subjects each in R/R DLBCL, FL, MCL, or PCNSL, in order to determine the RP2D. The combination of Compound 1 and rituximab is tested in subjects with R/R DLBCL or R/R FL.

Compound 1 is administered orally once daily (QD) on planned dosing days. Part B expansion cohorts tests different doses and/or schedules of Compound 1 based on the safety and tolerability determined in Part A. All treatments are administered in 28-day cycles until clinically-significant disease progression, unacceptable toxicity, or subject/physician decision to withdraw.

In Part A, each subject receives the assigned dose of Compound 1 on Cycle 1 Day 1 and daily on planned dosing days thereafter. The starting dose/schedule of Compound 1 is 0.4 mg/day starting on Day 1 for 5 consecutive days followed by 2 days off study drug every 7 days (5/7-day schedule) in each 28-day cycle. If the starting dose/schedule is not tolerated, a lower dose or less intense schedule may be explored. Provisional dose levels for Compound 1 in Part A include 0.1 mg (does level −2), 0.2 mg (does level −1), 0.4 mg (does level 1), 0.6 mg (does level 2), 0.8 mg (does level 3), 1.2 mg (does level 4), and 1.6 mg (does level 5). Alternate dosing schedules based on review of available clinical safety, PK and PD data may be explored, including, e.g., starting on Day 1 for 7 consecutive days followed by 7 days off study drug every 14 days (7/14-day schedule) in each 28-day cycle; starting on Day 1 for 5 consecutive days followed by 9 days off study drug every 14 days (5/14-day schedule) in each 28-day cycle; starting on Day 1 for 14 consecutive days followed by 14 days off study drug every 28 days (14/28-day schedule) in each 28-day cycle; and starting on Day 1 for 21 consecutive days followed by 7 days off study drug every 28 days (21/28-day schedule) in each 28-day cycle.

Following completion of dose escalation (Part A), selected expansion cohorts of approximately 20 efficacy evaluable subjects per cohort receive Compound 1 alone or in combination with rituximab. Expansion may occur at the MTD established in the Part A and/or at a lower dose, or an alternative tolerable dosing schedule, based on review of available safety, PK, and PD data.

The study is conducted in compliance with International Conference on Harmonisation (ICH) Good Clinical Practices (GCPs).

Study Population:

Subjects (male or female), ≥18 years of age, with R/R NHL who have relapsed after, progressed on (or not been able to tolerate due to medical comorbidities or unacceptable toxicity) standard anticancer therapy, or for whom no other approved conventional therapy exists, are enrolled in the study.

Inclusion Criteria: Subjects must satisfy the following criteria to be enrolled in the study:

1. Subject is ≥18 years of age at the time of signing the informed consent form (ICF).

2. Subject must understand and voluntarily sign an ICF prior to any study-related assessments/procedures being conducted.

3. Subject is willing and able to adhere to the study visit schedule and other protocol requirements.

4. Subject has a history of NHL (including DLBCL, FL, MCL, and PCNSL) with relapsed or refractory disease according to one of the following definitions:

a. For R/R DLBCL (de novo): following at least 2 prior lines of therapy OR have failed at least one prior line of standard therapy and are not eligible for SCT. Subjects with only one prior line of standard therapy must be ineligible for autologous SCT at the time of enrollment.

b. For R/R DLBCL (transformed lymphoma): following chemotherapy for lower grade lymphoma and at least one standard treatment regimen for DLBCL.

c. For R/R FL: following at least 2 prior lines of therapy and meet treatment criteria at the time of enrollment based on investigator's assessment (e.g., according to Groupe d'Etude des Lymphomes Folliculaires [GELF] criteria [National Comprehensive Cancer Network. NCCN Clinical Practice Guidelines in Oncology: B-cell Lymphomas; V.2.2018. 2018 Feb. 26; V.2. Available from: https://www.nccn.org/professionals/physician_gls/pdf/b-cell.pdf]).

d. For R/R MCL in Part B: following at least 2 prior lines of therapy.

e. For R/R PCNSL in Part B: following at least 2 prior lines of therapy.

5. Subjects must have measurable disease:

a. Bi-dimensionally measurable disease on cross sectional imaging by computed tomography (CT) or magnetic resonance imaging (MRI) with at least one lesion >1.5 cm in the transverse diameter, as defined by the Lugano classification of NHL (Cheson B D, Fisher R I, Barrington S F, Cavalli F, Schwartz L H, Zucca E, et al. Recommendations for initial evaluation, staging, and response assessment of Hodgkin and non-Hodgkin lymphoma: the Lugano classification. *J Clin Oncol.* 2014; 32(27):3059-3068).

Measurable disease cannot be previously irradiated.

b. PCNSL subjects in Part B must have disease that is objectively measurable by International Workshop to Standardize Baseline Evaluation and Response Criteria in Primary CNS Lymphoma (Abrey L E, Batchelow T T, et al. Baseline Evaluation and Response Criteria for Primary CNS Lymphoma. *JCO:* 2005, (23): 5034-5043), cerebrospinal fluid (CSF) cytology (in case of leptomeningeal only disease), or vitreal aspiration cytology and/or retinal photographs (in case of ocular lymphoma if clinically indicated).

6. Subject consents to retrieve formalin-fixed paraffin-embedded (FFPE) archival tumor tissue, either in tumor blocks or sectioned/mounted specimens, if collected within the last year and if using in place of the Screening biopsy for PD in Part A.

7. For subjects participating in Part A, subject consents to and has tumor accessible for tumor biopsy or FNA at Screening and FNA in Cycle 1; for Part B, subject consents to and has tumor accessible for paired tumor biopsies during Screening and Cycle 1.

8. Subject has an Eastern Cooperative Oncology Group (ECOG) performance status of 0, 1 or 2.

9. Subjects must have the following laboratory values:

a. Absolute neutrophil count (ANC)≥1.5×10$^9$/L without growth factor support for 7 days (14 days if pegfilgrastim).

b. Hemoglobin (Hgb)≥8 g/dL.

c. Platelets (plt)≥75×10$^9$/L without transfusion for 7 days.

d. Aspartate aminotransferase/serum glutamic oxaloacetic transaminase (AST/SGOT) and alanine aminotransferase/serum glutamate pyruvic transaminase (ALT/SGPT)≤2.5× upper limit of normal (ULN).

e. Serum bilirubin ≤1.5×ULN except in cases of Gilberts Syndrome, then ≤2.0×ULN.

f. Estimated serum creatinine clearance of ≥60 mL/min using the Cockcroft-Gault equation or directly determined from the 24-hour urine collection method.

g. International normalized ratio (INR)≤1.5×ULN and partial thromboplastin time (aPTT)<1.5×ULN.

10. Subjects must agree not to donate blood while receiving Compound 1, during dose interruptions and for at least 28 days following the last dose of Compound 1.

11. Females of childbearing potential (FCBP) must adhere to Pregnancy Prevention Plan requirements, including:

a. Either commit to true abstinence from heterosexual contact (which must be reviewed on a monthly basis and source documented) or agree to use, and be able to comply with, at least 2 effective contraceptive methods (oral, injectable, or implantable hormonal contraceptive; tubal ligation; intra-uterine device; barrier contraceptive with spermicide; or vasectomized partner), one of which must be barrier, from signing the ICF, at least 28 days before starting Compound 1, throughout the study, and for up to 28 days following the last dose of Compound 1 and up to one year following the last dose of rituximab; and b. Have 2 negative pregnancy tests as verified by the Investigator prior to starting Compound 1:

a negative serum pregnancy test (sensitivity of at least 25 mIU/mL) at Screening (between 10 to 14 days prior to Cycle 1 Day 1).

a negative serum or urine pregnancy test (Investigator's discretion) within 24 hours prior to Cycle 1 Day 1 of study treatment (note that the Screening serum pregnancy test can be used as the test prior to Day 1 study treatment if it is performed within the prior 24 hours).

c. Avoid conceiving for 28 days after the last dose of Compound 1.

d. Agree to ongoing pregnancy testing during the course of the study, and after the end of study treatment. This applies even if the subject practices true abstinence from heterosexual contact. (True abstinence is acceptable when this is in line with the preferred and usual lifestyle of the subject. In contrast, periodic abstinence (e.g., calendar, ovulation, symptothermal, post-ovulation methods) and withdrawal are not acceptable methods of contraception.)

e. Agree to refrain from donating ova while on Compound 1 for 30 days after its discontinuation.

f. Agree to abstain from breastfeeding or providing breast milk while on Compound 1 and for 28 days after its discontinuation.

12. Males must adhere to Pregnancy Prevention Plan requirements including the practice of true abstinence (which must be reviewed on a monthly basis) or agree to use a condom (a latex condom is recommended) during sexual contact with a pregnant female or a FCBP and avoid conceiving from the date of signing the ICF, while participating in the study, during dose interruptions, and for at least 90 days following Compound 1 discontinuation, even if he has undergone a successful vasectomy.

a. Males must agree to refrain from donating semen or sperm while on Compound 1 and for 90 days after its discontinuation.

Exclusion Criteria:

The presence of any of the following excludes a subject from enrollment:

1. Subject has any significant medical condition, laboratory abnormality, or psychiatric illness that would prevent the subject from participating in the study.

2. Subject has any condition including the presence of laboratory abnormalities, which places the subject at unacceptable risk if he/she were to participate in the study.

3. Subject has any condition that confounds the ability to interpret data from the study.

4. Subject has life expectancy ≤2 months.

5. Subjects who have aggressive lymphoma relapse requiring immediate cytoreductive therapy to avoid potential life-threatening consequences (e.g., due to tumor location).
6. Subject has received prior systemic anti-cancer treatment (approved or investigational) ≤5 half-lives or 4 weeks prior to starting Compound 1, whichever is shorter.
7. Subject has received prior CAR-T or other T-cell targeting treatment (approved or investigational)≤4 weeks prior to starting Compound 1.
8. Subject has received prior therapy with CRBN-modulating drug (e.g., lenalidomide, avadomide/CC-122, pomalidomide)≤4 weeks prior to starting Compound 1.
9. Subject is a pregnant or nursing female or intends to become pregnant during participation in the study.
10. Subject has symptomatic CNS involvement of disease (does not apply to PCNSL subjects in Part B).
11. Persistent diarrhea or malabsorption ≥Grade 2 National Cancer Institute (NCI) Common Terminology Criteria for Adverse Events (CTCAE), despite medical management.
12. Peripheral neuropathy ≥NCI CTCAE Grade 2.
13. Subject is on chronic systemic immunosuppressive therapy or corticosteroids (e.g., prednisone or equivalent not to exceed 10 mg per day within the last 14 days) or subjects with clinically significant graft-versus-host disease (GVHD).
　a. Stable use of inhaled corticosteroids is allowed.
　b. The use of topical steroids for ongoing skin or ocular GVHD is permitted.
　c. In Part B, PCNSL subjects taking glucocorticoids are allowed but must be on a stable dose for 7 days prior to Cycle 1 Day 1.
14. Subject has impaired cardiac function or clinically significant cardiac diseases, including any of the following:
　a. Left ventricular ejection fraction (LVEF)<45% as determined by multigated acquisition scan (MUGA) or echocardiogram (ECHO).
　b. Complete left bundle branch or bifascicular block.
　c. Congenital long QT syndrome.
　d. Persistent or clinically meaningful ventricular arrhythmias.
　e. QTcF≥470 msec on Screening electrocardiogram (ECG; mean of triplicate recordings).
　f. Unstable angina pectoris or myocardial infarction ≤3 months prior to starting.
15. Subject had prior autologous SCT≤3 months prior to starting Compound 1. If subject had prior autologous SCT>3 months prior to the start of Compound 1, any treatment-related toxicity is unresolved (grade >1).
16. Subject had prior allogeneic SCT with either standard or reduced intensity conditioning ≤6 months prior to starting Compound 1. If subject had prior allogeneic SCT>6 months prior to the start of Compound 1, any treatment-related toxicity is unresolved (grade >1).
17. Subject had major surgery ≤2 weeks prior to starting Compound 1. Subjects must have recovered from any clinically significant effects of recent surgery.
18. Prior radiotherapy within one month prior to starting study drug.
19. Subject has known human immunodeficiency virus (HIV) infection.
20. Subject has known chronic active hepatitis B or C virus (HBV/HCV) infection.
21. Subject has a history of concurrent second cancers requiring active, ongoing systemic treatment.
22. Concurrent administration of strong CYP3A4/5 modulators.

Length of Study:

The total study duration is expected to be approximately 4 to 5 years. Approximately 18 months are required to enroll and evaluate subjects in the dose escalation portion of the study (Part A). Approximately 12 to 18 months are required to enroll subjects in the Part B portion of the study. Completion of active treatment and post-treatment follow-up is expected to take an additional 12 to 24 months. The End of Trial is defined as either the date of the last visit of the last subject to complete the post-treatment follow-up, or the date of receipt of the last data point from the last subject that is required for primary, secondary and/or exploratory analysis, as pre-specified in the protocol, whichever is the later date.

Study Treatments: Subjects are assigned to a dose level and cohort by the Sponsor based on the subject's eligibility and slot availability. Subjects assigned to Dose Levels in Part A and single agent cohorts receive Compound 1 as a monotherapy. Subjects assigned to Part B combination cohorts receive Compound 1 in combination with rituximab. Compound 1 is supplied as capsules for oral administration in appropriate dose strengths.

For subjects receiving rituximab in combination with Compound 1 in Part B, rituximab is administered (per package insert and institutional standard practice) on planned dosing days at the fixed dose of 375 mg/m$^2$. In Cycle 1, rituximab is given on Days 1, 8, 15, and 22; in Cycles 2-6, rituximab is given on Day 1 of each cycle, thereafter, rituximab is given once every 8 weeks thereafter (e.g., C8D1, C10D1, etc.) until disease progression.

Overview of Key Efficacy Assessments:

The primary efficacy variable is tumor response rate. Tumor responses are determined by the Investigator. For NHL, the International Workshop Criteria for Malignant Lymphoma (Cheson B D, et al. Recommendations for initial evaluation, staging, and response assessment of Hodgkin and non-Hodgkin lymphoma: the Lugano classification. *J Clin Oncol.* 2014; 32(27):3059-3068) and the Deauville Criteria for fluorodeoxyglucose-positron emission tomography (FDG-PET) scan interpretation (Itti E, et al. An international confirmatory study of the prognostic value of early PET/CT in diffuse large B-cell lymphoma: comparison between Deauville criteria and DeltaSUVmax. *Eur J Nucl Med Mol Imaging.* 2013 September; 40(9):1312-20; Meignan M, et al. Report on the 4th International Workshop on Positron Emission Tomography in Lymphoma held in Menton, *France,* 3-5 Oct. 2012. *Leuk Lymphoma.* 2014 January; 55(1):31-37) are used for efficacy assessment ("Lugano criteria"). Other response criteria are used as appropriate, including the International Workshop to Standardize Baseline Evaluation and Response Criteria in Primary CNS Lymphoma (Abrey L E, et al. Baseline Evaluation and Response Criteria for Primary CNS Lymphoma. JCO: 2005, (23): 5034-5043) for PCNSL. Efficacy variables to be analyzed include tumor response at the end of treatment, the proportion of subjects alive and progression-free, and duration of response.

Efficacy assessments include: clinical findings (e.g., physical examination, constitutional symptoms), contrast enhanced computed tomography (CT) scans where appropriate, FDG-PET/CT scans where appropriate, bone marrow examination (biopsy and aspiration) where appropriate, and magnetic resonance imaging (MRI) where appropriate.

All treated subjects are included in the efficacy analyses.

A descriptive analysis of evidence of antitumor activity is provided based on clinical, laboratory, and radiographic assessments by the Investigator, which includes assessment of target lesions, non-target lesions, new lesions and overall response.

The efficacy variable of focus for Part A is objective response rate (ORR). Additional efficacy variables to be analyzed include time to response, duration of response, progression-free survival (PFS) and overall survival (OS).

Efficacy variables mature when the last subject in each cohort has withdrawn from the study or completed one year of treatment.

Secondary and exploratory endpoints include evaluation of Compound 1 PD and predictive biomarkers in blood and/or tumor, and exploration of PK, PD, toxicity, and activity relationships.

Overview of Key Safety Assessments:

Safety assessments include: monitoring for adverse events (AEs), physical examination, vital signs/weight, Eastern Cooperative Oncology Group (ECOG) performance status, safety laboratory assessments (including hematology and clinical chemistry, coagulation studies, and urinalysis), cardiac monitoring including 12-lead electrocardiograms (ECGs) and left ventricular ejection fraction (LVEF) assessments, concomitant medications, procedures, and therapies, and pregnancy testing (for females of child bearing potential [FCBP]).

Overview of Pharmacokinetic Assessments:

The PK profiles of Compound 1 are determined from serial blood collections.

A number of references have been cited, the disclosures of which are incorporated herein by reference in their entirety.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating non-Hodgkin lymphoma (NHL), comprising administering to a subject having NHL a therapeutically effective amount of Compound 3 of the formula:

3 or an enantiomer, mixture of enantiomers, tautomer, or pharmaceutically acceptable salt thereof, wherein the NHL is follicular lymphoma (FL), mantle cell lymphoma (MCL) or primary central nervous system lymphoma (PCNSL).

2. A method of treating non-Hodgkin lymphoma (NHL), comprising administering to a subject having NHL a therapeutically effective amount of Compound 1 of the formula:

1 or a tautomer, or pharmaceutically acceptable salt thereof, wherein the NHL is follicular lymphoma (FL), mantle cell lymphoma (MCL) or primary central nervous system lymphoma (PCNSL).

3. A method of treating non-Hodgkin lymphoma (NHL), comprising administering to a subject having NHL a therapeutically effective amount of Compound 2 of the formula:

2 or a tautomer, or pharmaceutically acceptable salt thereof, wherein the NHL is follicular lymphoma (FL), mantle cell lymphoma (MCL) or primary central nervous system lymphoma (PCNSL).

4. The method of claim 2, wherein the NHL is follicular lymphoma (FL).

5. The method of claim 2, wherein the NHL is mantle cell lymphoma (MCL).

6. The method of claim 2, wherein the NHL is primary central nervous system lymphoma (PCNSL).

7. The method of claim 2, wherein the NHL is relapsed or refractory NHL.

8. The method of claim 7, wherein the NHL is relapsed or refractory follicular lymphoma.

9. The method of claim 7, wherein the NHL is relapsed or refractory mantle cell lymphoma.

10. The method of claim 7, wherein the NHL is relapsed or refractory primary central nervous system lymphoma.

11. The method of claim 7, wherein the subject has failed at least one prior therapy.

12. The method of claim 2, wherein the NHL is newly diagnosed.

13. The method of claim 2, wherein the compound is administered orally.

14. The method of claim 2, wherein the compound is administered once daily for 5 days followed by 2 days of rest.

15. The method of claim 2, wherein the compound is administered once daily for 5 days followed by 9 days of rest.

16. The method of claim 2, wherein the compound is administered once daily for 7 days followed by 7 days of rest.

17. The method of claim 2, wherein the compound is administered once daily for 10 days followed by 4 days of rest.

18. The method of claim 2, wherein the compound is administered once daily for 14 days followed by 14 days of rest.

19. The method of claim 2, wherein the compound is administered once daily for 21 days followed by 7 days of rest.

20. The method of claim 2, wherein the compound is administered on days 1 to 5 of a 7-day cycle, on days 1 to 5 of a 14-day cycle, on days 1 to 7 of a 14-day cycle, on days 1 to 10 of a 14-day cycle, on days 1 to 14 of a 28-day cycle, on days 1 to 21 of a 28-day cycle, on days 1 to 5, days 8 to 12, days 15 to 19, and days 22 to 26 of a 28-day cycle, on days 1 to 5 and days 15 to 19 of a 28-day cycle, on days 1 to 7 and days 15 to 21 of a 28-day cycle, or on days 1 to 10 and days 15 to 24 of a 28-day cycle.

21. The method of claim 2, wherein the compound is administered in an amount of about 0.1 mg, about 0.2 mg, about 0.4 mg, about 0.6 mg, about 0.8 mg, about 1.2 mg or about 1.6 mg per day.

22. The method of claim 2, further comprising administering to the subject a therapeutically effective amount of rituximab.

23. The method of claim 22, wherein rituximab is administered intravenously.

24. The method of claim 23, wherein rituximab is administered at a dose of about 375 mg/m$^2$.

25. The method of claim 22, wherein rituximab is administered once every 7 days, once every 4 weeks, or once every 8 weeks.

26. The method of claim 22, comprising (i) administering rituximab on days 1, 8, 15, and 22 of the first 28-day cycle ("Cycle 1"), on day 1 of the second to the sixth 28-day cycles, and then once every 8 weeks; and (ii) administering Compound 1 in cycles of once daily for 5 days followed by 2 days of rest, starting on day 1 of Cycle 1.

27. The method of claim 22, comprising (i) administering rituximab on days 1, 8, 15, and 22 of the first 28-day cycle ("Cycle 1"), on day 1 of the second to the sixth 28-day cycles, and then once every 8 weeks; and (ii) administering Compound 1 in cycles of once daily for 5 days followed by 9 days of rest, starting on day 1 of Cycle 1.

28. The method of claim 22, comprising (i) administering rituximab on days 1, 8, 15, and 22 of the first 28-day cycle ("Cycle 1"), on day 1 of the second to the sixth 28-day cycles, and then once every 8 weeks; and (ii) administering Compound 1 in cycles of once daily for 7 days followed by 7 days of rest, starting on day 1 of Cycle 1.

29. The method of claim 22, comprising (i) administering rituximab on days 1, 8, 15, and 22 of the first 28-day cycle ("Cycle 1"), on day 1 of the second to the sixth 28-day cycles, and then once every 8 weeks; and (ii) administering Compound 1 in cycles of once daily for 10 days followed by 4 days of rest, starting on day 1 of Cycle 1.

30. The method of claim 22, comprising (i) administering rituximab on days 1, 8, 15, and 22 of the first 28-day cycle ("Cycle 1"), on day 1 of the second to the sixth 28-day cycles, and then once every 8 weeks; and (ii) administering Compound 1 in cycles of once daily for 14 days followed by 14 days of rest, starting on day 1 of Cycle 1.

31. The method of claim 22, comprising (i) administering rituximab on days 1, 8, 15, and 22 of the first 28-day cycle ("Cycle 1"), on day 1 of the second to the sixth 28-day cycles, and then once every 8 weeks; and (ii) administering Compound 1 in cycles of once daily for 21 days followed by 7 days of rest, starting on day 1 of Cycle 1.

* * * * *